US008481700B2

(12) United States Patent
Vlassenbroeck et al.

(10) Patent No.: US 8,481,700 B2
(45) Date of Patent: Jul. 9, 2013

(54) DETECTION OF MAGE-A EXPRESSION

(75) Inventors: Ilse Vlassenbroeck, Sart-Tilman (BE); Katja Bierau, Wolfshausen (DE)

(73) Assignees: MDxHealth SA (BE); GlaxoSmithKline Biologicals SA (BE)

( * ) Notice: Subject to any disclaimer, the term of this patent is extended or adjusted under 35 U.S.C. 154(b) by 167 days.

(21) Appl. No.: 12/678,702

(22) PCT Filed: Sep. 17, 2008

(86) PCT No.: PCT/GB2008/003142
§ 371 (c)(1),
(2), (4) Date: Jul. 16, 2010

(87) PCT Pub. No.: WO2009/037438
PCT Pub. Date: Mar. 26, 2009

(65) Prior Publication Data
US 2010/0280105 A1 Nov. 4, 2010

Related U.S. Application Data

(60) Provisional application No. 60/960,128, filed on Sep. 17, 2007.

(51) Int. Cl.
C07H 21/04 (2006.01)
C12Q 1/68 (2006.01)

(52) U.S. Cl.
USPC ... 536/23.1; 536/24.3; 536/24.33; 536/24.31; 435/6.1; 435/6.11; 435/6.12; 435/91.1; 435/91.2

(58) Field of Classification Search
None
See application file for complete search history.

(56) References Cited

U.S. PATENT DOCUMENTS

| 4,437,975 | A | 3/1984 | Gillespie et al. |
| 6,090,552 | A | 7/2000 | Nazarenko et al. |
| 6,410,276 | B1 | 6/2002 | Burg et al. |
| 6,426,217 | B1 | 7/2002 | Chaux et al. |
| 6,768,000 | B1 * | 7/2004 | Nardone ............... 536/22.1 |
| 2006/0194208 | A1 * | 8/2006 | Tetzner et al. ............ 435/6 |

FOREIGN PATENT DOCUMENTS

| EP | 1491639 | | 12/2004 |
| EP | 1491639 | * | 3/2005 |
| WO | 9006995 | | 6/1990 |
| WO | 9118926 | | 12/1991 |
| WO | 9400153 | | 1/1994 |
| WO | 9517210 | | 6/1995 |
| WO | 9602555 | | 2/1996 |
| WO | 9633739 | | 10/1996 |
| WO | 9850399 | | 11/1998 |
| WO | 9940188 | | 8/1999 |
| WO | 0009159 | | 2/2000 |
| WO | 0021551 | | 4/2000 |
| WO | 0062800 | | 10/2000 |
| WO | 0134617 | | 5/2001 |
| WO | 03046142 | | 6/2003 |
| WO | 03065806 | | 8/2003 |
| WO | 04067726 | | 8/2004 |
| WO | 2007147876 | | 12/2007 |

OTHER PUBLICATIONS

NEB catalog (1996/1997), pp. 111.*
Qiu et al. (Clinical Biochemistry, vol. 39, pp. 259-266, 2006).*
Chomez et al., "An Overview of the MAGE Gene Family with the Identification of All Human Members of the Family", Cancer Research, Jul. 15, 2001, 61:5544-5551.
Eads et al., "MethyLight: a high-throughput assay to measure DNA methylation", Nucleic Acids Research, 2000, 28 (8):e33, I-VIII.
Esteller et al., "A Gene Hypermethylation Profile of Human Cancer", Cancer Research, Apr. 15, 2001, 61:3225-3229.
Frommer et al., "A genomic sequencing protocol that yields a positive display of 5-methylcytosine residues in individual DNA strands", Proceedings of the National Academy of Science, Mar. 1992, 89:1827-1831.
Hoffman et al., "Causes and consequences of DNA hypomethylation in human cancer", Biochemistry and Cell Biology, 2005, 83:296-321.
Honda et al., "Demethylation of MAGE promoters during gastric cancer progression", British Journal of Cancer, 2004, 90:838-843.
Kim et al., "Promoter hypomethylation and reactivation of MAGE-A1 and MAGE-A3 genes in colorectal cancer cell lines and cancer tissues", World Journal of Gastroenterology, Sep. 2006, 12(35):5651-5657.
Lucas et al., "Identification of a New MAGE Gene with Tumor-specific Expression by Representational Difference Analysis", Cancer Research, Feb. 15, 1998, 58:743-752.
Lucas et al., "A New MAGE Gene with Ubiquitous Expression Does Not Code for Known MAGE Antigens Recognized by T Cells", Cancer Research, Aug. 15, 1999, 59:4100-4103.
Lucas et al., "MAGE-B5, MAGE-B6, MAGE-C2, and MAGE-C3: Four new members of the MAGE family with tumor-specific expression", International Journal of Cancer, 2000, 87:55-60.
Mikeska et al., "Optimization of Quantitative MGMT Promoter Methylation Analysis Using Pyrosequencing and combined Bisulfite Restriction Analysis", Journal of Molecular Diagnostics, Jul. 2007, 9(3):368-381.
Muscatelli et al., "Isolation and characterization of a MAGE gene family in the Xp21.3 region", Proceedings of the National Academy of Science, May 1995, 92:4987-4991.

(Continued)

*Primary Examiner* — Jeanine A Goldberg
(74) *Attorney, Agent, or Firm* — Andrus, Sceales, Starke & Sawall, LLP

(57) ABSTRACT

An oligonucleotide, primer or probe comprises the nucleotide sequences of any of SEQ ID NO. 5, 6, 7, 2, 3, 4, 8, 9, 11, 12, 13, 14, 15, 16, 17, 18, 19 or 25. The oligonucleotides are useful for the detection of the methylation status of a gene, in particular the MAGE-A3 gene. The oligonucleotides are useful in primer pairs, kits and methods for determining the methylation status of the MAGE-A3 gene and for diagnosing cancer, directing therapy and selecting subjects for treatment. The primer or probe can comprise a loop or hairpin structure and can be used in real-time methylation specific PCR.

6 Claims, 16 Drawing Sheets

OTHER PUBLICATIONS

Takahashi et al., "Identification of MAGE-1 and MAGE-4 Proteins in Spermatogonia and Primary Spermatocytes of Testis", Cancer Research, Aug. 15, 1995, 55:3478-3482.

Vansteenkiste et al., Abstract of "Final results of a multi-center, double-blind, randomized, placebo-controlled phase II study to assess the efficacy of MAGE-A3 immunotherapeutic as adjuvant therapy in stage IB/II non-small cell lung cancer (NSCLC)", Journal of Clinical Oncology, Jun. 20, 2007 Supplement of ASCO Annual Meeting Proceedings, 25(18S):7554.

Zammatteo et al., "DNA Microarray to Monitor the Expression of MAGE-A Genes", Clinical Chemistry, 2002, 48 (1):25-34.

Furuta et al., "Promoter methylation profiling of 30 genes in human malignant melanoma", Cancer Science, Dec. 2004, 95(12):962-968.

Jang et al., "Activation of melanoma antigen tumor antigens occurs early in lung carcinogenesis", Cancer Research, Nov. 1, 2001, 61(21):7959-7963.

Maxwell et al., "Quantitative analysis of 06-alkylguanine-DNA alkyltransferase in malignant glioma", Molecular Cancer Therapeutics, Oct. 2006, 5(10):2531-2539.

Qui et al., "5' CpG island methylation analysis identifies the MAGE-A1 and MAGE-A3 genes as potential markers of HCC", Clinical Biochemistry, Mar. 1, 2006, 39(3):259-266.

Rickert et al., "Refinement of single-nucleotide polymorphism genotyping methods on human genomic DNA: amplifluor allele-specific polymerase chain reaction versus ligation detection reaction-TaqMan", Analytical Biochemistry, 2006, 330(2):288-297.

Tetzner, "Entwicklung von Realtime-PCR-Methoden. zur Analyse von DNA-Methylierung", 2006, 1-122.

Tetzner, "Real-time PCR methods for methylation analysis", 2006, (English Translation), 1.3.1-1.3.4.

Vlassenbroeck et al., "Validation of real-time methylation-specific PCR to determine 0 <6>-methylguanine-DNA methyltransferase gene promoter methylation in flioma", Journal of Molecular Diagnostics, Jan. 1, 2008, 10 (4):332-337.

International Search Report for PCT/GB2008/003142 dated Jan. 22, 2009.

Written Opinion for PCT/GB2008/003142 dated Jan. 22, 2009.

\* cited by examiner

MAGEA3_GO_1_U
MAGEA3_GO_2_U
MAGEA3_FURUTA_U
MAGEA3_QIU_U
■: transcription start site CATGCTTACCTCCACCCCCATCCGATCCCCATCCAGGCA
GAATCCAGTTCCACCCCTGCCCGGAACCCAGGGTAGTAC
CGTTGCCAGGATGTGACGCCACTGACTTGCGCAT
TGGAGGTCAGAAGACCGC■AGATTCTCGCCCTGAGCAA
CGAGCGACGGCCTGACGTCGGCGGAGGGAAGCCG
GCCCAGGCTCGGTGAGGAG (SEQ ID NO. 10)

FIG. 1a

TATGTTTATTTTTATTTTTATTTGATTTTTATTTAGGTAGA
ATTTAGTTTTATTTTTGTTTGGAATTTAGGGTAGTATTGTT
GTTAGGATGTGATGTTATTGATTTGTGTATTGGAG
GTTAGAAGATTGT■AGATTTTTGTTTTGAGTAATGAGT
GATGGTTTGATGTTGGTGGAGGGAAGTTGGTTTAGG
TTTGGTGAGGAG (SEQ ID NO. 41)

FIG. 1b

MAGE-A3_GO_2 U (118bp)

CATGCTTACCTCCACCCCATCCGATCCCCATCCAGGCAGAATCC
AGTTCCACCCCTGCCCGGAACCCAGGGTAGTACCGTTGCCAGG
ATGTGACGCCACTGACTTGCGCATTGGAGGTCAGAAGACCGCGA
GATTCTCGCCCTGAGCAACGAGCGACGGCCTGACGTCGGCGGA
GGGAAGCCGGCCCAGGCTCGGTGAGGAG

FIG. 2a

MAGE-A3_GO_2 U (118bp)

TATGTTTATTTTTATTTTTATTTGATTTTTATTTAGGTAGAATTTAG
TTTTATTTTTGTTTGGAATTTAGGGTAGTATTGTTGTTAGGATGT
GATGTTATTGATTTGTGTATTGGAGGTTAGAAGATTGTGAGATTT
TTGTTTTGAGTAATGAGTGATGGTTTGATGTTGGTGGAGGGAAG
TTGGTTTAGGTTTGGTGAGGAG(

FIG. 2b

| | GO_1 U assay | GO_2 U assay | Furuta U assay | Qiu U assay |
|---|---|---|---|---|
| Area under the ROC curve (AUC) | 0.912 | 0.971 | 0.939 | 0.944 |
| Standard error | 0.0455 | 0.0258 | 0.0377 | 0.0361 |
| 95% Confidence interval | 0.781 to 0.977 | 0.863 to 0.996 | 0.817 to 0.989 | 0.824 to 0.990 |
| Significance level P (Area=0.5) | 0.0001 | 0.0001 | 0.0001 | 0.0001 |

FIG. 6e

|  | GO_1 U assay | GO_2 U assay (second run) | Furuta U assay | Qiu U assay |
|---|---|---|---|---|
| Area under the ROC curve (AUC) | 0.954 | 0.971 | 0.949 | 0.948 |
| Standard error | 0.03 | 0.0238 | 0.0316 | 0.032 |
| 95% Confidence interval | 0.868 to 0.990 | 0.893 to 0.996 | 0.861 to 0.988 | 0.859 to 0.988 |
| Significance level P (Area=0.5) | 0.0001 | 0.0001 | 0.0001 | 0.0001 |

FIG. 7e

| | GO_1 U assay | GO_2 U assay (second run) | Furuta U assay | Qiu U assay |
|---|---|---|---|---|
| Area under the ROC curve (AUC) | 0.933 | 0.932 | 0.923 | 0.912 |
| Standard error | 0.0376 | 0.0377 | 0.0401 | 0.0428 |
| 95% Confidence interval | 0.825 to 0.984 | 0.826 to 0.983 | 0.813 to 0.979 | 0.799 to 0.973 |
| Significance level P (Area=0.5) | 0.0001 | 0.0001 | 0.0001 | 0.0001 |

FIG. 8e

Protein D-MAGE-A3-His
(SEQ ID NO:40)

M<u>D</u>KTLALSL LAAGVLAGCS SHSSNMANTQ MKSDKIIIAH RGASGYLPEH - 50
TLESKALAFA QQADYLEQDL AMTKDGRLVV IHDHFLDGLT DVAKKFPHRH -100
RKDGRYYVID FTLKEIQSLE MTENFETM<u>D</u>L EQRSQHCKPE EGLEARGEAL -150
GLVGAQAPAT EEQEAASSSS TLVEVTLGEV PAAESPDPPQ SPQGASSLPT -200
TMNYPLWSQS YEDSSNQEEE GPSTFPDLES EFQAALSRKV AELVHFLLLK -250
YRAREPVTKA EMLGSVVGNW QYFFPVIFSK ASSSLQLVFG IELMEVDPIG -300
HLYIFATCLG LSYDGLLGDN QIMPKAGLLI IVLAIIAREG DCAPEEKIWE -350
ELSVLEVFEG REDSILGDPK KLLTQHFVQE NYLEYRQVPG SDPACYEFLW -400
GPRAIVETSY VKVLHHMVKI SGGPHISYPP LHEWVLREGE E<span style="background-color:lightgray">GG</span>HHHHHHH*-450

SINGLE UNDERLINED = first 109 amino acids of Protein D
DOUBLE UNDERLINED= Protein D signal sequence (18 aa)
Boxed = inserted/substituted sequences: Met-Asp at 2-3 (substituted);
Met-Asp at 128-129(inserted) and Gly-Gly at 442-443 (inserted)
Bold = fragment of MAGE3: amino acids 3-314 of MAGE3 (312 AA total)
Grey = 7 his tail

FIG. 10

DETECTION OF MAGE-A EXPRESSION

CROSS-REFERENCE TO RELATED APPLICATIONS

This application is the U.S. national stage application of International Application PCT/GB2008/003142, filed Sep. 17, 2008, which international application was published on Mar. 26, 2009, as International Publication WO2009/037438 in the English language. The International Application claims priority of U.S. Provisional Patent Application No. 60/960, 128 filed Sep. 17, 2007.

FIELD OF THE INVENTION

The present invention is concerned with the detection of MAGE-A family gene expression. More specifically, the invention relates to methods of detecting methylated or unmethylated forms of MAGE-A3 and associated oligonucleotides, primers, probes, primer pairs and kits. The methods of the invention involve amplification techniques, in particular fluorescence based real-time and end-point PCR methods, and have diagnostic, prognostic and therapeutic utility.

BACKGROUND TO THE INVENTION

MAGE genes belong to the family of cancer/testis antigens. The MAGE family of genes comprises over 20 members and is made up of MAGE A, B, C and D genes (Scanlan et al, (2002) Immunol Rev. 188:22-32; Chomez et al, (2001) Cancer Res. 61(14):5544-51). They are clustered on chromosome X (Lucas et al., 1998 Cancer Res. 58.743-752; Lucas et al., 1999 Cancer Res 59:4100-4103; Lucas et al., 2000 Int J Cancer 87:55-60; Lurquin et al., 1997 Genomics 46:397-408; Muscatelli et al., 1995 Proc Natl Acad Sci USA 92:4987-4991; Pold et al., 1999 Genomics 59:161-167; Rogner et al 1995 Genomics 29:725-731), and have a yet undefined function (Ohman et al 2001 Exp Cell Res. 265(2): 185-94). The MAGE genes are highly homologous and the members of the MAGE-A family, especially, have between 60-98% homology.

The human MAGE-A3 gene is expressed in various types of tumours, including melanoma (Furuta et al. 2004 Cancer Sci. 95, 962-968.), bladder cancer, hepatocellular carcinoma (Qiu et al. 2006. Clinical Biochemistry 39, 259-266), gastric carcinoma (Honda et al. 2004 British Journal of Cancer 90, 838-843), colorectal cancer (Kim et al. 2006 World Journal of Gastroenterology 12, 5651-5657) and lung cancer (NSCLC) (Scanlan et al 2002 Immunol Rev. 188:22-32; Jang et al 2001 Cancer Res. 61, 21: 7959-7963). No expression has been observed in any normal adult tissues with the only exception of testicular germ cells or placenta (Haas et al. 1988 Am J Reprod Immunol Microbial 18:47-51; Takahashi et al. 1995 Cancer Res 55:3478-382).

Antigen-Specific Cancer Immunotherapeutics (ASCI) represent a novel class of medicines designed to train the immune system to recognize and eliminate cancer cells in a highly specific manner. As such, ASCI allow targeted treatment. ASCI have two principal components: "tumor antigens" to direct the immune response specifically against the cancer cell and "adjuvant systems" that comprise immunostimulation compounds selected to increase the anti-tumour immune response. MAGE-A3 antigen and constructs suitable for use in ASCI are described in WO99/40188 and encouraging phase II study results with MAGE-A3 ASCI in patients with Non Small Lung Cancer (NSCLC) have been reported recently (J. Clin. Oncol. Vol. 25, No. 18S (June 20 Suppl.) 2007: 7554).

It is important to have quantitative high throughput assays capable of specifically identifying MAGE-A3-expressing patients that would benefit from immunotherapy, monitoring MAGE-A3 expression for dosage purpose, identifying Mage-A3 expressing samples in clinical trials, or simply identify at an early stage patients with cancer. A number of applicable diagnostic methods have been described and include: Semi-quantitative RT-PCR (De Plaen et al. 1994 Immunogenetics 40(5):360-9), other PCR based techniques and low-density microarrays (Zammatteo et al. 2002 Clinical Chemistry 48(1) 25-34). Further, an improved RT-PCR method for use in conjunction with MAGE-A3 ASCI has been discussed in WO2007/147876.

The greatest disadvantage of the existing assays is that they require RNA isolation to assess MAGEA3 expression. Formalin-Fixed, Paraffin-Embedded (FFPE) tumour tissue is the usual method of tumour tissue preservation within clinical centres. The fixation in formalin changes the structure of molecules of RNA within the tissue, causing cross linking and also partial degradation. The partial degradation leads to the creation of smaller pieces of RNA of between 100-300 base pairs. These structural changes to the RNA limit the use of RNA extracted from FFPE tissue to measure MAGEA3 expression levels.

An object of the present invention is to provide an improved assay that eliminates the disadvantages of the existing assays.

Gene methylation is an important regulator of gene expression. In particular, methylation at cytosine residues found in CpG di-nucleotide pairs in the promoter region of specific genes can contribute to many disease conditions through down regulation of gene expression. For example, aberrant methylation of tumour suppressor genes can lead to up or down regulation of these genes and is thus associated with the presence and development of many cancers (Hoffmann et al. 2005 Biochem Cell Biol 83: 296-321). Patterns of aberrant gene methylation are often specific to the tissue of origin. Accordingly, detection of the methylation status of specific genes may be of prognostic and diagnostic utility and can be used to both determine the relative stage of a disease and also to predict response to certain types of therapy (Laird. 2003 Nat Rev Cancer 3: 253-266).

Methylation-Specific PCR (MSP) with visualization of the results on a gel (gel-based MSP assay) is widely used to determine epigenetic silencing of genes (Esteller M et al. Cancer Res 2001; 61:3225-9.), although quantitative tests using other technologies have been developed (Laird P W., Nat Rev Cancer 2003; 3:253-66; Eads et al. Nucleic Acids Res 2000; 28:E32; Mikeska T, et al. J Mol Diagn 2007).

A number of fluorescence based technologies are available for real-time monitoring of nucleic acid amplification reactions. One such technology is described in U.S. Pat. No. 6,090,552 and EP 0912597 and is commercially known as Amplifluor®. This method is also suitable for end-point monitoring of nucleic acid amplification reactions. Vlassenbroeck et al. (Vlassenbroeck et al., 2008. Journal of Molec. Diagn., V10, No. 4) further describes a standardized direct, real-time MSP assay with use of the Amplifluor® technology.

SUMMARY OF THE INVENTION

The present invention relates to improved methods and/or assays of measuring MAGE-A3 expression. The present invention further relates to certain types of therapy, in particular Antigen-Specific Cancer Immunotherapeutics (ASCI) based treatment of patients identified as expressing MAGE-A3 through use of oligonucleotides, primers, probes, primer pairs, kits and/or methods as described herein. MAGE-A3 protein expression is detected by determining the methylation status of the MAGE-A3 gene rather than measuring the expression level of the gene itself. The inventors show that the methylation status result of their methylation tests is in good concordance with results obtained with the RT-PCR assay that established the predictive value of the MAGE-A3 expression in NSCLC for benefit from MAGE-A3 immunotherapy. The assays are thus useful for selecting patients suitable for treatment, for predicting the likelihood of successful treatment of a patient and can be used to aid patient therapy selection.

In one aspect, the present invention provides an oligonucleotide, primer or probe comprising or consisting essentially of or consisting of the nucleotide sequence of any SEQ ID NO. 2, 3, 4, 5, 6, 7, 8, 9, 11, 12, 13, 14, 15, 16, 17, 18, 19 or 25 which oligonucleotide, primer or probe is useful for the detection of the methylation status of a gene.

The oligonucleotide, primer or probe preferably comprises, consists essentially of or consists of the following contiguous sequences in 5' to 3' order:
  (a) a first nucleotide sequence of between approximately 6 and 30 nucleotides, wherein a nucleotide within said first nucleotide sequence is labelled with a first moiety selected from the donor moiety and the acceptor moiety of a molecular energy transfer pair, wherein the donor moiety emits fluorescence at one or more particular wavelengths when excited, and the acceptor moiety absorbs and/or quenches said fluorescence emitted by said donor moiety;
  (b) a second, single-stranded nucleotide sequence comprising, consisting essentially of or consisting of between approximately 3 and 20 nucleotides;
  (c) a third nucleotide sequence comprising, consisting essentially of or consisting of between approximately 6 and 30 nucleotides, wherein a nucleotide within said third nucleotide sequence is labelled with a second moiety selected from said donor moiety and said acceptor moiety, and said second moiety is the member of said group not labelling said first nucleotide sequence, wherein said third nucleotide sequence is complementary in reverse order to said first nucleotide sequence such that a duplex can form between said first nucleotide sequence and said third nucleotide sequence such that said first moiety and second moiety are in proximity such that, when the donor moiety is excited and emits fluorescence, the acceptor moiety absorbs and quenches said fluorescence emitted by said donor moiety; and
  (d) at the 3' end of the primer, a fourth, single-stranded nucleotide sequence comprising, consisting essentially of or consisting of between approximately 8 and 40 nucleotides that comprises at its 3' end the nucleotide sequence of any of SEQ ID NO. 2, 4, 5, 7, 8, 11, 13, 14, 16, 17, 19 or 25;
  wherein when said duplex is not formed, said first moiety and said second moiety are separated by a distance that prevents molecular energy transfer between said first and second moiety.

The specific nucleotide sequences at the 3' end permit the methylation status of the MAGE-A3 gene to be determined. These primers bind preferentially to unmethylated forms of the MAGEA3 gene following treatment with an appropriate reagent (as discussed herein). Properties of these oligonucleotides are discussed herein, which discussion applies mutatis mutandis. The specific nucleotide sequences are able to prime synthesis by a nucleic acid polymerase of a nucleotide sequence complementary to a nucleic acid strand comprising the portion of the methylated or unmethylated DNA of the MAGE A family gene.

Most preferably, the oligonucleotide, primer or probe consists of the nucleotide sequence of SEQ ID NO. 3, 6, 9, 12, 15 or 18 and is used to amplify a portion of the gene of interest.

Further provided is a primer pair comprising a primer comprising or consisting essentially of or consisting of the nucleotide sequence of any SEQ ID NO. 2, 3, 4, 5, 6, 7, 8, 9, 11, 12, 13, 14, 15, 16, 17, 18, 19 or 25.

In a further aspect, there is provided a kit comprising at least one primer, primer pair or set of primers comprising or consisting essentially of or consisting of the nucleotide sequence of any SEQ ID NO. 2, 3, 4, 5, 6, 7, 8, 9, 11, 12, 13, 14, 15, 16, 17, 18, 19 or 25. The kit is for detecting the methylation status of a gene, in particular a MAGE-A family gene such as MAGE-A3.

In a further aspect, the invention provides for a method of detecting the methylation status of the Mage-A3 gene in a DNA-containing sample, comprising:
  (a) contacting/treating the DNA-containing sample with a reagent which selectively modifies unmethylated cytosine residues in the DNA to produce detectable modified residues but which does not modify methylated cytosine residues
  (b) amplifying at least a portion of the methylated or unmethylated gene of interest using at least one primer pair, at least one primer of which is designed to bind only to the sequence of methylated or unmethylated DNA respectively following treatment with the reagent, wherein at least one primer in the primer pair comprises, consists essentially of, or consists of a the nucleotide sequence of any of SEQ ID NO. 2, 3, 4, 5, 6, 7, 8, 9, 11, 12, 13, 14, 15, 16, 17, 18, 19 or 25 (as appropriate).

In a further aspect, there is provided a method of diagnosing cancer or predisposition to cancer comprising detecting the methylation status of the MAGE-A3 gene in a sample by using an oligonucleotide, primer or probe, primer pair, kit or a method as described herein, wherein the presence of unmethylated MAGE-A3 in the sample is indicative for cancer or predisposition to cancer.

In a further aspect, there is provided a method for determining the presence of MAGE-A3 positive tumor comprising detecting the methylation status of the MAGE-A3 gene in a sample by using an oligonucleotide, primer or probe, primer pair, kit or a method as described herein, wherein the presence of unmethylated MAGE-A3 is indicative for the presence of a MAGE-A3 positive tumor. By "MAGE-A3 positive tumor" is meant any tumor or tumor cells (isolated from a patient) which express the MAGE-A3 antigen.

The invention further provides a method for identifying and/or selecting a patient suitable for treatment with a MAGE-A3 immunotherapeutic comprising detecting the methylation status of the MAGE-A3 gene in a sample of the patient by using an oligonucleotide, primer or probe, primer pair, kit or a method as described herein, wherein if the MAGE-A3 gene is unmethylated the subject is (preferably) identified and/or selected for treatment with the MAGE-A3 immunotherapeutic. Thus, patients with unmethylated MAGEA3 are preferred to those in which the gene is methylated.

Alternatively, if the gene is not unmethylated the subject is preferably not identified and/or selected for treatment with a MAGE-A3 immunotherapeutic.

In a related aspect, the invention provides a method for predicting the likelihood of successful treatment of cancer comprising detecting the methylation status of the MAGE-A3 gene in a sample of the patient by using an oligonucleotide, primer or probe, primer pair, kit or a method as described herein, wherein if the gene is unmethylated the likelihood of successful treatment with a MAGE-A3 immunotherapeutic is higher than if the gene is methylated.

Alternatively, the absence of unmethylated MAGE-A3 in the sample indicates that the likelihood of resistance to treatment with a MAGE-A3 immunotherapeutic is higher than if the gene is unmethylated. Thus, the detection of a methylated MAGE-A3 gene indicates that the probability of successful treatment with an immunotherapeutic is low.

In a further related aspect, the invention provides a method of selecting a suitable treatment regimen for cancer comprising detecting the methylation status of the MAGE-A3 gene in a sample of the patient by using an oligonucleotide, primer or probe, primer pair, kit or a method as described herein, wherein if the gene is unmethylated, an immunotherapeutic is selected for treatment.

Alternatively, if the gene is not unmethylated, treatment with an immunotherapeutic is contra-indicated.

Also provided is a method of treating cancer in a subject comprising administration of an immunotherapeutic, wherein the subject has been selected for treatment on the basis of measuring the methylation status of a MAGE-A3 gene, according to any of the methods of the invention or by using an oligonucleotide, primer or probe, primer pair, kit or a method as described herein.

Preferably, for all of the different aspects described herein, the detection of unmethylated MAGE-A3 gene corresponds to an increased level of MAGE-A3 protein.

The present invention further provides a method of treating a patient comprising: measuring the methylation status of a MAGE-A3 gene according to any of the methods of the invention by using an oligonucleotide, primer or probe, primer pair, kit or a method as described herein, and then administering to the patient a composition comprising MAGE-A3 as described herein. The composition is preferably administered if the MAGE-A3 gene is found to be unmethylated.

In a further aspect there is provided a method of treating a patient susceptible to recurrence of a MAGE-A3 expressing tumour, the patient having been treated to remove tumour tissue, the method comprising: measuring the methylation status of a MAGE-A3 gene in the tumour tissue, according to any of the methods of the invention or by using an oligonucleotide, primer or probe, primer pair, kit or a method as described herein, and then administering to the patient a composition comprising MAGE-A3 as described herein. The composition is preferably administered if the MAGE-A3 gene is found to be unmethylated.

In a still further aspect of the present invention there is provided a use of a composition comprising MAGE-A3 in the manufacture of a medicament for the treatment of a patient suffering from a tumour, in which a patient has been selected for treatment on the basis of measuring the methylation status of a MAGE-A3 gene, according to any of the methods of the invention or by using an oligonucleotide, primer or probe, primer pair, kit or a method as described herein. There is also provided a composition comprising MAGE-A3 for use in the treatment of a patient suffering from a tumour, in which a patient has been selected for treatment on the basis of measuring the methylation status of a MAGE-A3 gene, according to any of the methods of the invention or by using an oligonucleotide, primer or probe, primer pair, kit or a method as described herein.

In a yet further embodiment there is provided a use of a composition comprising MAGE-A3 in the manufacture of a medicament for the treatment of a patient susceptible to recurrence of a MAGE-A3 expressing tumour, in which a patient has been selected for treatment on the basis of measuring the methylation status of a MAGE-A3 gene, according to any of the methods of the invention or by using an oligonucleotide, primer or probe, primer pair, kit or a method as described herein. There is also provided a composition comprising MAGE-A3 for use in the treatment of a patient susceptible to recurrence of a MAGE-A3 expressing tumour, in which a patient has been selected for treatment on the basis of measuring the methylation status of a MAGE-A3 gene, according to any of the methods of the invention or by using an oligonucleotide, primer or probe, primer pair, kit or a method as described herein.

DETAILED DESCRIPTION OF THE INVENTION

The invention provides an assay for detecting the presence and/or amount of a methylated or unmethylated MAGE-A3 gene in a DNA-containing sample. To develop this assay, it was necessary to identify regions susceptible to methylation in the MAGE-A3 gene and to develop particular oligonucleotides that could differentiate unmethylated from methylated forms of the MAGE-A3 gene.

Accordingly, in a first aspect, the invention provides oligonucleotides comprising, consisting essentially of, or consisting of the nucleotide sequence of any SEQ ID NO. 2, 3, 4, 5, 6, 7, 8, 9, 11, 12, 13, 14, 15, 16, 17, 18, 19 or 25. These oligonucleotides are useful in the detection of the methylation status of a gene of interest. The oligonucleotides may serve as primers and/or probes. In certain embodiments, the oligonucleotides detect the unmethylated form to the gene. Suitable oligonucleotides to detect the unmethylated form comprise, consist essentially of, or consist of the nucleotide sequence of any of SEQ ID NO. 2, 4, 5, 7, 8, 11, 13 or 25. Suitable oligonucleotides to detect the methylated form comprise, consist essentially of, or consist of the nucleotide sequence of any SEQ ID NO. 14, 16, 17 or 19. In certain embodiments, these oligonucleotides comprise a hairpin structure as described in the present invention. Such preferred oligonucleotides include the sequences according to SEQ ID NO. 3, 6, 9, and 12 for detecting the unmethylated form of the gene and SEQ ID NO. 15 and 18 for detecting the methylated form of the gene.

The "genes" or "gene of interest" of the invention are preferably MAGEA3 and/or MAGEA6 genes. MAGEA3 and MAGEA6 are the gene symbols approved by the HUGO Gene Nomenclature Committee. The MAGEA3 gene is located on chromosome X (location q28) and the gene sequence is listed under the accession numbers NM_005362 and ENSG00000197172. The MAGE-A3 gene encodes melanoma antigen family A, 3. The MAGEA6 gene is located on chromosome X (location q28). MAGE-A3 is often referred to interchangeably as MAGE-3 or MAGEA3. Likewise, MAGE-A6 is often referred to interchangeably as MAGE-6 or MAGEA6; all are used herein. Hypomethylation of these genes may be linked to the incidence of cancers, such as melanoma or lung cancer (including NSCLC) for example.

CpG dinucleotides susceptible to methylation are typically concentrated in the promoter region of human genes. In a preferred embodiment, the methylation status of the gene is assessed by determining levels of methylation in the promoter region of the gene. A "promoter" is a region upstream from the transcription start site (TSS), extending between approximately 10 Kb, 3Kb, 1 Kb, 500 bp or 150 to 300 bp from the TSS. For MAGE-3, the CpG distribution in the promoter region is rather scarce.

The term "methylation state" or "methylation status" refers to the presence or absence of 5-methylcytosine ("5-mCyt") at one or a plurality of CpG dinucleotides within a DNA sequence. "Hypermethylation" is defined as an increase in the level of methylation above normal levels. Thus, it relates to aberrant methylation of cytosine (5-mCyt) at specific CpG sites in a gene, often in the promoter region. Normal levels of methylation may be defined by determining the level of methylation in non-cancerous cells for example.

"Hypomethylation" refers to a decreased presence of 5-mCyt at one or a plurality of CpG dinucleotides within a DNA sequence (of a test DNA sample), relative to the amount of 5-mCyt found at corresponding CpG dinucleotides within a "normal" DNA sequence (found in a suitable control sample). Again, "normal" levels of methylation may be defined by determining the level of methylation in non-cancerous cells for example. In this invention, hypomethylation of the MAGE-A3 and/or MAGE-A6 gene is indicative of an increased expression of this tumour associated antigen gene which provides a reliable indicator of cancer.

The invention provides in a second aspect for a method of detecting the presence and/or amount of a methylated or unmethylated gene in a DNA-containing sample comprising the step of contacting the DNA-containing sample with at least one oligonucleotide comprising, consisting essentially of, or consisting of the nucleotide sequence of any SEQ ID NO. 2, 3, 4, 5, 6, 7, 8, 9, 11, 12, 13, 14, 15, 16, 17, 18, 19 or 25. The method preferably comprises the further step of assessing whether the gene is methylated or unmethylated. This may depend upon whether the oligonucltide stably binds to the DNA in the DNA-containing sample, as discussed herein.

Techniques for assessing methylation status are based on distinct approaches. Any suitable technique, applying the oligonucleotides of the invention may be employed. In one embodiment, approaches for detecting methylated CpG dinucleotide motifs use a reagent which selectively modifies unmethylated cytosine residues in the DNA to produce detectable modified residues. The reagent does not modify methylated cytosine residues and thus allows for discrimination between unmethylated and methylated nucleic acid molecules in a downstream process, which preferably may involve nucleic acid amplification. The reagent may, in one embodiment, act to selectively deaminate unmethylated cytosine residues. Thus, following exposure to the reagent the unmethylated DNA contains a different nucleotide sequence to that of corresponding methylated DNA. The deamination of cytosine results in a uracil residue being present, which has the same base pairing properties as thymine, which differs from cytosine base pairing behaviour. This makes the discrimination between methylated and non-methylated cytosines possible.

Useful conventional techniques for assessing sequence differences use oligonucleotide primers. Two approaches to primer design are possible. Firstly, primers may be designed that themselves do not cover any potential sites of DNA methylation. Sequence variations at sites of differential methylation are located between the two primer binding sites and visualisation of the sequence variation requires further assay steps. Secondly, primers may be designed that hybridize specifically with either the methylated or unmethylated version of the initial treated sequence. After hybridization, an amplification reaction can be performed and amplification products assayed using any detection system known in the art. The presence of an amplification product indicates that the primer hybridized to the DNA. The specificity of the primer indicates whether the DNA had been modified or not, which in turn indicates whether the DNA had been methylated or not. If there is a sufficient region of complementarity, e.g., 12, 13, 14, 15, 16, 17, 18, 19, 20, 21 or 22 nucleotides, to the target, then the primer may also contain additional nucleotide residues that do not interfere with hybridization but may be useful for other manipulations. Examples of such other residues may be sites for restriction endonuclease cleavage, for ligand binding or for factor binding or linkers or repeats, or residues for purpose of visualization. The oligonucleotide primers may or may not be such that they are specific for modified methylated residues. Preferred oligonucleotides for use as primers comprise, consist essentially of, or consist of the nucleotide sequence of any of SEQ ID NO. 2, 3, 4, 5, 6, 7, 8, 9, 11, 12, 13, 14, 15, 16, 17, 18, 19 or 25.

A further way to distinguish between modified and unmodified nucleic acid is to use oligonucleotide probes. Such probes may hybridize directly to modified nucleic acid or to further products of modified nucleic acid, such as products obtained by amplification. Probe-based assays exploit the oligonucleotide hybridisation to specific sequences and subsequent detection of the hybrid. There may also be further purification steps before the amplification product is detected e.g. a precipitation step. Oligonucleotide probes may be labeled using any detection system known in the art. These include but are not limited to fluorescent moieties, radioisotope labelled moieties, bioluminescent moieties, luminescent moieties, chemiluminescent moieties, enzymes, substrates, receptors, or ligands. Preferred oligonucleotides for use as probes comprise, consist essentially of, or consist of the nucleotide sequence of any of SEQ ID NO. 2, 4, 5, 7, 8, 11, 13, 14, 16, 17, 19 or 25.

"Oligonucleotide primer" is referred to herein interchangeably as "primer". Likewise, "oligonucleotide probe" is referred to herein interchangeably as "probe".

In preferred embodiments, the methylation status of the gene (or portion thereof, especially the CpG islands) is determined using methylation specific PCR (MSP).

The MSP technique will be familiar to one of skill in the art. In the MSP approach, DNA may be amplified using primer pairs designed to distinguish unmethylated from methylated DNA by taking advantage of sequence differences as a result of sodium-bisulfite treatment (Herman J G et al. Proc Natl Acad Sci USA. 1996 Sep. 3; 93(18):9821-6 and WO 97/46705). A specific example of the MSP technique is designated real-time quantitative MSP (QMSP), which permits reliable quantification of methylated DNA in real time.

Real-time methods are generally based on the continuous optical monitoring of an amplification procedure and utilise fluorescently labelled reagents whose incorporation in a product can be quantified and whose quantification is indicative of copy number of that sequence in the template. Such labeled reagent may be a fluorescent dye that preferentially binds double-stranded DNA and whose fluorescence is greatly enhanced by binding of double-stranded DNA. Alternatively, labeled primers and/or labeled probes can be used. They represent a specific application of the well known and commercially available real-time amplification techniques such as TAQMAN®, MOLECULAR BEACONS®, AMPLIFLUOR® and SCORPION® DzyNA®, etc. Often, these real-time methods are used with the polymerase chain reaction (PCR).

TaqMan technology uses linear, hydrolytic oligonucleotide probes that contain a fluorescent dye and a quenching dye.

When irradiated, the excited fluorescent dye transfers energy to the nearby quenching dye molecule rather than fluoresencing (FRET principle). TaqMan probes anneal to an internal region of the PCR product and are cleaved by the exonuclease activity of the polymerase when it replicates a template. This ends the activity of the quencher, and the reporter dye starts to emit fluorescence which increases in each cycle proportional to the rate of probe cleavage.

Molecular beacons also contain fluorescent and quenching dyes, but they are designed to adopt a hairpin structure while free in solution to bring both dyes in close proximity for Fluorescence Resonance Energy Transfer (FRET) to occur. When the beacon hybridises to the target during the annealing step, the hairpin linearises and both dyes (donor and acceptor/quencher) are separated. The increase in fluorescence detected from the donor will correlate to the amount of PCR product available.

With scorpion probes, sequence-specific priming and PCR product detection is achieved using a single oligonucleotide. The scorpion probe maintains a stem-loop configuration in the unhybridized state and FRET occurs between the fluorophore and quencher. The 3' portion of the stem also contains a sequence that is complementary to the extension product of the primer. This sequence is linked to the 5' end of a specific primer via a non-amplifiable monomer. After extension of the scorpion primer, the specific probe sequence is able to bind to its complement within the extended amplicon, thus opening up the hairpin loop, separating the fluorophore and quencher, and providing a fluorescence signal.

In Heavymethyl, the priming is methylation specific, but non-extendable oligonucleotide blockers provide this specificity instead of the primers themselves. The blockers bind to bisulfite-treated DNA in a methylation-specific manner, and their binding sites overlap the primer binding sites. When the blocker is bound, the primer cannot bind and therefore the amplicon is not generated. Heavymethyl can be used in combination with real-time detection.

The Plexor™ qPCR and qRT-PCR Systems take advantage of the specific interaction between two modified nucleotides to achieve quantitative PCR analysis. One of the PCR primers contains a fluorescent label adjacent to an iso-dC residue at the 5' terminus. The second PCR primer is unlabeled. The reaction mix includes deoxynucleotides and iso-dGTP modified with the quencher dabcyl. Dabcyl-iso-dGTP is preferentially incorporated at the position complementary to the iso-dC residue. The incorporation of the dabcyl-iso-dGTP at this position results in quenching of the fluorescent dye on the complementary strand and a reduction in fluorescence, which allows quantitation during amplification. For these multiplex reactions, a primer pair with a different fluorophore is used for each target sequence.

Thus the oligonucleotides comprising, consisting essentially of, or consisting of the nucleotide sequence of any SEQ ID NO. 2, 3, 4, 5, 6, 7, 8, 9, 11, 12, 13, 14, 15, 16, 17, 18, 19 or 25 may be employed as primers or probes in the aforementioned methods for detection of the methylation status of a gene of interest.

In a preferred embodiment, the invention provides a real-time method of detecting the presence and/or amount of a methylated or unmethylated gene of interest in a DNA-containing sample, comprising:
(a) contacting/treating the DNA-containing sample with a reagent which selectively modifies unmethylated cytosine residues in the DNA to produce detectable modified residues but which does not modify methylated cytosine residues
(b) amplifying at least a portion of the methylated or unmethylated gene of interest using at least one primer pair, at least one primer of which is designed to bind only to the sequence of methylated or unmethylated DNA respectively following treatment with the reagent, wherein at least one primer in the primer pair comprises, consists essentially of, or consists of the nucleotide sequence of any of SEQ ID NO. 2, 3, 4, 5, 6, 7, 8, 9, 11, 12, 13, 14, 15, 16, 17, 18 or 19.

The gene of interest in the methods of the invention is preferably the MAGE-A3 and/or the MAGEA6 gene. Preferably, at least one primer in the primer pair is a primer containing a stem loop structure carrying a donor and an acceptor moiety of a molecular energy transfer pair arranged such that in the absence of amplification, the acceptor moiety quenches fluorescence emitted by the donor moiety (upon excitation) and during amplification, the stem loop structure is disrupted so as to separate the donor and acceptor moieties sufficiently to produce a detectable fluorescence signal. This may be detected in real-time to provide an indication of the presence of the methylated or unmethylated gene of interest. The primer in the primer pair which comprises, consists essentially of, or consists of the nucleotide sequence of any of SEQ ID NO. 2, 3, 4, 5, 6, 7, 8, 9, 11, 12, 13, 14, 15, 16, 17, 18 or 19 preferably carries the stem loop structure.

In certain embodiments the gene copy number of the methylated or unmethylated gene is determined. Here, the method described herein preferably comprises a further step:
(c) quantifying the results of the real-time detection against a standard curve for the methylated or unmethylated gene of interest to produce an output of gene copy number.

Preferably, step (c) is further characterised in that the amplification is considered valid where the cycle threshold value is less than 40.

For genes such as the MageA3 and/or MageA6 gene, detection of an unmethylated version of the gene may be of primary relevance.

The methods of the invention allow the presence of a methylated or unmethylated gene of interest to be detected in a sample in real-time. Since the methods of the invention are quantitative methods, the (relative) amounts of the methylated or unmethylated form of the gene of interest can also be determined as the reaction proceeds. Real-time methods do not need to be utilised, however. Analyses can be performed only to discover whether the target DNA is present in the sample or not. End-point amplification detection techniques utilize the same approaches as widely used for Real Time PCR. Therefore, the methods of the invention may encompass an end-point method of detecting the presence and/or amount of a methylated or unmethylated gene of interest in a DNA-containing sample.

Thus, the invention provides a (n end point) method of detecting the presence and/or amount of a methylated or unmethylated gene of interest in a DNA-containing sample, comprising:
(a) contacting and/or treating the DNA-containing sample with a reagent which selectively modifies unmethylated cytosine residues in the DNA to produce detectable modified residues but which does not modify methylated cytosine residues
(b) amplifying at least a portion of the methylated or unmethylated gene of interest using at least one primer pair, at least one primer of which is designed to bind only to the sequence of methylated or unmethylated DNA respectively following treatment with the reagent, wherein at least one primer in the primer pair comprises, consists essentially of, or consists of the nucleotide sequence of any of SEQ ID NO. 2, 3, 4, 5, 6, 7, 8, 9, 11, 12, 13, 14, 15, 16, 17, 18, 19 or 25.

As aforementioned, the gene of interest in the methods of the invention is preferably the MAGE-A3 and/or MAGE-A6 gene. Preferably, at least one primer in the primer pair is a primer containing a stem loop structure carrying a donor and an acceptor moiety of a molecular energy transfer pair having the characteristics as described herein. The primer in the primer pair which comprises, consists essentially of, or consists of the nucleotide sequence of any of SEQ ID NO. 2, 3, 4, 5, 6, 7, 8, 9, 11, 12, 13, 14, 15, 16, 17, 18 or 19 preferably carries the stem loop structure.

For the MAGE-A3 and/or MAGE-A6 gene, detection of an unmethylated version of the gene may be of primary relevance. Primers comprising, consisting essentially of, or consisting of the nucleotide sequence of any of SEQ ID NO. 2, 3, 4, 5, 6, 7, 8, 9, 11, 12, 13 or 25 have been designed for the purpose of detecting unmethylated MAGEA3 DNA following treatment with the reagent.

The absence of unmethylated gene will indicate the presence of methylated gene. However, the detection of methylated gene is also within the scope of the invention. Primers comprising, consisting essentially of, or consisting of the nucleotide sequence of any SEQ ID NO. 14, 15, 16, 17, 18 or 19 have been designed for the purpose of detecting methylated MAGEA3 DNA following treatment with the reagent.

In case a gene copy number of the methylated or unmethylated gene is desired, the method preferably comprises a further step:

(c) quantifying the results of the detection against a standard curve for the methylated or unmethylated gene of interest to produce an output of gene copy number.

All embodiments of the invention are applicable to the end-point aspects of the invention and thus apply mutatis mutandis. End point analysis may invoke use of a fluorescent plate reader or other suitable instrumentation to determine the fluorescence at the end of the amplification.

The methods of the invention are most preferably ex vivo or in vitro methods carried out on any suitable (DNA containing) test sample. In one embodiment, however, the method may also include the step of obtaining the sample. The test sample is a DNA-containing sample, in particular a DNA-containing sample including the gene of interest. The methods of the invention can be used in the diagnosis of disease, in particular where methylation of a gene of interest is (known to be) linked to the incidence of disease.

The DNA-containing sample may comprise any suitable tissue sample or body fluid. Preferably, the test sample is obtained from a human subject. For cancer applications, the sample may comprise a tissue sample taken from the tissue suspected of being cancerous or from a representative bodily fluid.

Hypomethylation of the MAGE-A3 gene has been associated with lung cancer. Thus, in one embodiment, the test sample to be used in the methods of the invention involving a MAGE-A3 gene preferably contains lung cells or nucleic acid from lung cells. Most preferably, the sample is a Formalin Fixed Paraffin Embedded (FFPE) tissue. There are two types of lung cancer: non-small cell lung cancer (NSCLC) and small cell lung cancer (SCLC). The names simply describe the type of cell found in the tumours. The test sample preferably contains cells or nucleic acid from non-small cell lung carcinoma (NSCLC). NSCLC includes squamous-cell carcinoma, adenocarcinoma, and large-cell carcinoma and accounts for around 80% of lung cancers. In a preferred embodiment, where the cancer is a NSCLC, the sample is a lung tissue sample or a sputum sample. NSCLC is hard to cure and treatments available tend to have the aim of prolonging life as far as possible and relieving symptoms of disease. NSCLC is the most common type of lung cancer and is associated with poor outcomes.

Hypomethylation of the MAGE-A3 gene is also linked to bladder cancer. Thus, in additional embodiments, a further preferred test sample to be used in the methods of the invention contains transitional bladder cells or squamous carcinoma bladder cells. Preferably, the test sample is obtained from a bladder tissue. More preferably, it is derived from urine and contains nucleic acid from transitional bladder cells or squamous carcinoma bladder cells. The test sample can be derived from liquid urine, a precipitate thereof, or a precipitate in the urine. The tissues and body fluids can be collected using any suitable method, many of which are well known in the art.

Hypomethylation of the MAGE-A3 gene is also linked to melanoma. Melanoma is a pigmented, readily accessible lesion that has been well defined in histopathological terms. Early radial growth phase (RGP) melanomas can invade into the epidermis and papillary dermis, but have no capacity for metastasis; resection at this stage is almost completely curative. A subsequent vertical growth phase (VGP) denotes a transition to a more aggressive stage, which is capable of metastasis. Changes in gene expression occurring at the RGP/VGP transition are, thus, of great interest. Thus, in additional embodiments, a further preferred test sample to be used in the methods of the invention contains melanoma cells. Preferably, the test sample is obtained from a skin lesion.

Other DNA-containing samples for use in the methods of the invention include samples for diagnostic, prognostic, or personalised medicinal uses. These samples may be obtained from surgical samples, such as biopsies or fine needle aspirates, from paraffin embedded tissues, from frozen tumor tissue samples, from fresh tumour tissue samples or from a fresh or frozen body fluid, for example. Non-limiting examples include whole blood, bone marrow, cerebrospinal fluid, peritoneal fluid, pleural fluid, lymph fluid, serum, plasma, urine, chyle, stool, ejaculate, sputum, nipple aspirate, saliva, swabs specimens, colon wash specimens and brush specimens. The tissues and body fluids can be collected using any suitable method, many such methods are well known in the art. Assessment of a paraffin-embedded specimen can be performed directly or on a tissue section. The terms "sample", "patient sample" and "sample of the patient" are used interchangeably and are intended to mean a DNA-containing sample from a patient, as described above.

The methods of the invention may be carried out on purified or unpurified DNA-containing samples. However, in a preferred embodiment, prior to step (a) (the reagent treatment step) or as a preliminary step, DNA is isolated/extracted/purified from the DNA-containing sample. Any suitable DNA isolation technique may be utilised. Examples of purification techniques may be found in standard texts such as Molecular Cloning—A Laboratory Manual (Third Edition), Sambrook and Russell (see in particular Appendix 8 and Chapter 5 therein). In one preferred embodiment, purification involves alcohol precipitation of DNA. Preferred alcohols include ethanol and isopropanol. Suitable purification techniques also include salt-based precipitation methods. Thus, in one specific embodiment the DNA purification technique comprises use of a high concentration of salt to precipitate contaminants. The salt may comprise, consist essentially of or consist of potassium acetate and/or ammonium acetate for example. The method may further include steps of removal of contaminants which have been precipitated, followed by recovery of DNA through alcohol precipitation.

In an alternative embodiment, the DNA purification technique is based upon use of organic solvents to extract contaminants from cell lysates. Thus, in one embodiment, the method comprises use of phenol, chloroform and isoamyl alcohol to extract the DNA. Suitable conditions are employed to ensure that the contaminants are separated into the organic phase and that DNA remains in the aqueous phase. Further kits use magnetic beads, silica-membrane, etc. Such kits are well known in the art and commercially available. The methods of the invention may use the PUREGENE® DNA Purification Kit.

In preferred embodiments of these purification techniques, extracted DNA is recovered through alcohol precipitation, such as ethanol or isopropanol precipitation.

Formalin-Fixed, Paraffin-Embedded (FFPE) tumour tissue is the usual method of tumour tissue preservation within clinical centres. Such FFPE embedded samples require a dewaxing step prior to DNA extraction. In a preferred embodiment, FFPE tissue samples or sample material immobilized on slides are first dewaxed by xylene treatment. The contact period with the xylene should be sufficient to allow the xylene to contact and interact with the sample. In a more preferred embodiment, FFPE samples are deparaffinized in 100% xylene for about 2 hours. This step may be repeated once more to ensure complete deparaffinization. After xylene treatment samples are rehydrated using 70% ethanol.

The methods of the invention may also, as appropriate, incorporate (also prior to step (a) or as a preliminary step) quantification of isolated/extracted/purified DNA in the sample. Quantification of the DNA in the sample may be achieved using any suitable means. Quantitation of nucleic acids may, for example, be based upon use of a spectrophotometer, a fluorometer or a UV transilluminator. Examples of suitable techniques are described in standard texts such as Molecular Cloning—A Laboratory Manual (Third Edition), Sambrook and Russell (see in particular Appendix 8 therein). In a preferred embodiment, kits such as the Picogreen® dsDNA quantitation kit available from Molecular Probes, Invitrogen may be employed to quantify the DNA.

The methods of the invention rely upon a reagent which selectively modifies unmethylated cytosine residues in the DNA to produce detectable modified residues. The mode of action of the reagent has been explained already. In a preferred embodiment, the reagent which selectively modifies unmethylated cytosine residues in the DNA to produce detectable modified residues but which does not modify methylated cytosine residues comprises, consists essentially of or consists of a bisulphite reagent (Frommer et al., Proc. Natl. Acad. Sci. USA 1992 89:1827-1831,). Several bisulphite containing reagents are known in the art and suitable kits for carrying out the deamination reaction are commercially available (such as the EZ DNA methylation kit from Zymo Research). A particularly preferred reagent for use in the methods of the invention comprises, consists essentially of or consists of sodium bisulphite.

Once the DNA in the sample has been treated with the reagent, it is then necessary to detect the difference in nucleotide sequence caused by the reagent. This is done using a nucleic acid amplification technique. As mentioned already, functionally relevant methylation is most commonly associated with the promoter regions of genes. In particular, so called "CpG islands" include a relatively high incidence of CpG residues and are often found in the promoter region of the gene. Various software programs exist to allow CpG islands in a gene of interest to be identified. Accordingly, the methods of the invention may involve amplifying at least a portion of the methylated or unmethylated gene of interest using at least one primer pair. As discussed above, since the residues of interest whose methylation status is to be investigated, are typically found in defined CpG islands and/or in the promoter region of the gene of interest, the primer pair will typically amplify only a portion of the gene (in this region), rather than the entirety. Any suitable portion of the gene may be amplified according to the methods of the invention, provided that the amplification product is detectable as a reliable indicator of the presence of the gene of interest. Particularly readily detectable amplification products are between approximately 50 and 250 bp. Even more preferably, amplification using the at least one primer pair for amplification of the methylated or unmethylated gene of interest produces an amplification product of between approximately 100 and 200 bp or between 50 and 100 bp. This is particularly relevant for tissue samples, especially paraffin embedded samples where limited DNA quality is typically obtained and smaller amplicons may be desired. In a preferred embodiment, the detectable amplification product comprises at least the nucleotide sequence of any of SEQ ID NO. 2, 4, 5, 7, 8, 11, 13, 14, 16, 17 or 19. Preferably, an amplification product of (around) 100 bp, 110 bp, 115 bp, 120 bp, 125 bp, 126 bp, 130 bp, 135 bp, 140 bp or 142 bp is produced.

At least one primer in the primer pair, and preferably both primers, is designed to bind only to the sequence of methylated or unmethylated DNA following treatment with the reagent. Thus, the primer acts to discriminate between a methylated and an unmethylated gene by base pairing only with the either the methylated form of the gene (which remains unmodified following treatment with the reagent) or the unmethylated form of the gene (which is modified by the reagent) depending upon the application to which the methods are put. The primer must, therefore, cover at least one methylation site in the gene of interest. Preferably, the primer binds to a region of the gene including at least 1, 2, 3, 4, 5, 6, 7 or 8 methylation sites. Most preferably the primer is designed to bind to a sequence in which all cytosine residues in CpG pairs within the primer binding site are methylated or unmethylated—i.e. a "fully methylated" or a "fully unmethylated" sequence. However, if only a single or a few methylation sites are of functional relevance, the primer may be designed to bind to a target sequence in which only these residues must be methylated (remain as a cytosine) or unmethylated (converted to uracil) for effective binding to take place. Other (non-functionally relevant) potential sites of methylation may be avoided entirely through appropriate primer design or primers may be designed which bind independently of the methylation status of these less relevant sites (for example by including a mix of G and A residues at the appropriate location within the primer sequence). Accordingly, an amplification product is expected only if the methylated or unmethylated form of the gene of interest was present in the original DNA-containing sample. Additionally or alternatively, it may be appropriate for at least one primer in the primer pair to bind only to the sequence of unmethylated DNA following treatment with the reagent and the other primer to bind to methylated DNA only following treatment—for example where a gene involves functionally important sites which are methylated and separate functionally important sites which are unmethylated.

Preferably, at least one primer in the primer pair is a primer containing a stem loop or "hairpin" structure carrying a donor and an acceptor moiety of a molecular energy transfer pair. This primer may or may not be a primer which discriminates between methylated and unmethylated DNA as desired. The primer is arranged such that in the absence of amplification, the acceptor moiety quenches fluorescence emitted by the donor moiety upon excitation. Thus, prior to, or in the absence of, amplification directed by the primer the stem loop or "hairpin" structure remains intact. Fluorescence emitted by the donor moiety is effectively accepted by the acceptor moiety leading to quenching of fluorescence.

During amplification, the configuration of the stem loop or hairpin structure of the primer is altered. In particular, once the primer is incorporated into an amplification product, and in particular into a double stranded DNA, (particularly during the second round of amplification) the stem loop or hairpin structure is disrupted. This alteration in structure separates the donor and acceptor moieties sufficiently that the acceptor moiety is no longer capable of effectively quenching the fluorescence emitted by the donor moiety. Thus, the donor moiety produces a detectable fluorescence signal. This signal is detected in real-time to provide an indication of the gene copy number of the methylated or unmethylated gene of interest.

Thus, the methods of the invention may utilise oligonucleotides for amplification of nucleic acids that are detectably labelled with molecular energy transfer (MET) labels. The primers contain a donor and/or acceptor moiety of a MET pair and are incorporated into the amplified product of an amplification reaction, such that the amplified product contains both a donor and acceptor moiety of a MET pair.

When the amplified product is double stranded, the MET pair incorporated into the amplified product may be on the same strand or, when the amplification is triamplification, on opposite strands. In certain instances wherein the polymerase used in amplification has 5'-3' exonuclease activity, one of the MET pair moieties may be cleaved from at least some of the population of amplified product by this exonuclease activity. Such exonuclease activity is not detrimental to the amplification methods of the invention.

The methods of the invention, as discussed herein are adaptable to many methods for amplification of nucleic acid sequences, including polymerase chain reaction (PCR), tri-amplification, and other amplification systems.

In a preferred embodiment, the MET is fluorescence resonance energy transfer (FRET), in which the oligonucleotides are labelled with donor and acceptor moieties, wherein the donor moiety is a fluorophore and the acceptor moiety may be a fluorophore, such that fluorescent energy emitted by the donor moiety is absorbed by the acceptor moiety. The acceptor moiety may be a quencher. Thus, the amplification primer is a hairpin primer that contains both donor and acceptor moieties, and is configured such that the acceptor moiety quenches the fluorescence of the donor. When the primer is incorporated into the amplification product its configuration changes, quenching is eliminated, and the fluorescence of the donor moiety may be detected.

The methods of the invention permit detection of an amplification product without prior separation of unincorporated oligonucleotides. Moreover, they allow detection of the amplification product directly, by incorporating the labelled oligonucleotide into the product.

In a preferred embodiment, the methods of the invention also involve determining the expression of a reference gene. Reference genes are important to allow comparisons to be made between different samples. By selecting an appropriate gene believed to be expressed in a stable and reliable fashion between the samples to be compared, detecting amplification of a reference gene together with the gene of interest takes into account inter-sample variability, such as amount of input material, enzymatic efficiency, sample degradation etc. A reference gene should ideally, in the presence of a reliable amount of input DNA, be one which is constantly expressed between the samples under test. Thus, the results from the gene of interest can be normalised against the corresponding copy number of the reference gene. Suitable reference genes for the present invention include beta-actin, glyceraldehyde-3-phosphate dehydrogenase (GAPDH), ribosomal RNA genes such as 18S ribosomal RNA and RNA polymerase II gene (Radonic A. et al., Biochem Biophys Res Commun. 2004 Jan. 23; 313(4):856-62). In a particularly preferred embodiment, the reference gene is beta-actin.

Thus the methods of the invention may be further characterised in amplifying at least a portion of a reference gene using at least one primer pair, wherein at least one primer in the primer pair is a primer containing a stem loop structure having the aforementioned characteristics.

Any suitable portion of the reference gene may be amplified according to the methods of the invention, provided that the amplification product is detectable as a reliable indicator of the presence of the reference gene. Particularly readily detectable amplification products are between approximately 50 and 250 bp. Even more preferably, amplification using the at least one primer pair for amplification of the reference gene produces an amplification product of between approximately 100 and 200 bp. This is particularly relevant for tissue samples, especially paraffin embedded samples where limited DNA quality is typically obtained.

In the embodiments in which a reference gene is included in the methods of the invention the methods may be further characterised in that the step of the methods which comprises quantifying the results of the (real-time) detection against a standard curve for the methylated or unmethylated gene of interest also comprises quantifying the results of the real-time detection of the reference gene against a standard curve for the reference gene to produce an output of gene copy number in each case and optionally further comprises normalising the results by dividing the gene copy number of the methylated or unmethylated gene of interest by the gene copy number of the reference gene.

Again, the methods are characterised in that the amplification is considered valid where the cycle threshold value is less than 40. This is preferably the case for both the gene of interest and reference gene.

Amplification of at least a portion of the reference gene generally utilises at least one primer pair. Preferably, at least one primer in the primer pair is a primer containing a stem loop structure carrying a donor and an acceptor moiety of a molecular energy transfer pair, as for the gene of interest. The mode of action of such structure during amplification has been explained herein.

The "hairpin" primers for use in the methods of the invention are most preferably as described in U.S. Pat. No. 6,090,552 and EP 0912597, the disclosures of which are hereby incorporated in their entirety. These primers are commercially known as Amplifluor® primers. Thus, in a particularly preferred embodiment, the primer containing a stem loop structure used to amplify a portion of the gene of interest and/or reference gene comprises, consists essentially of or consists of the following contiguous sequences in 5' to 3' order:

(a) a first nucleotide sequence of between approximately 6 and 30 nucleotides, wherein a nucleotide within said first nucleotide sequence is labelled with a first moiety selected from the donor moiety and the acceptor moiety of a molecular energy transfer pair, wherein the donor moiety emits fluorescence at one or more particular wavelengths when excited, and the acceptor moiety absorbs and/or quenches said fluorescence emitted by said donor moiety;

(b) a second, single-stranded nucleotide sequence comprising, consisting essentially of or consisting of between approximately 3 and 20 nucleotides;

(c) a third nucleotide sequence comprising, consisting essentially of or consisting of between approximately 6 and 30 nucleotides, wherein a nucleotide within said third nucleotide sequence is labelled with a second moiety selected from said donor moiety and said acceptor moiety, and said second moiety is the member of said group not labelling said first nucleotide sequence, wherein said third nucleotide sequence is complementary in reverse order to said first nucleotide sequence such that a duplex can form between said first nucleotide sequence and said third nucleotide sequence such that said first moiety and second moiety are in proximity such that, when the donor moiety is excited and emits fluorescence, the acceptor moiety absorbs and quenches said fluorescence emitted by said donor moiety; and (d) at the 3' end of the primer, a fourth, single-stranded nucleotide sequence comprising, consisting essentially of or consisting of between approximately 8 and 40 nucleotides that comprises at its 3' end a sequence of any of SEQ ID NO. 2, 4, 5, 7, 8, 11, 13, 14, 16, 17, 19 or 25 (and thus able to prime synthesis by a nucleic acid polymerase of a nucleotide sequence complementary to a nucleic acid strand comprising the portion of the methylated or unmethylated DNA of the gene); wherein when said duplex is not formed, said first moiety and said second moiety are separated by a distance that prevents molecular energy transfer between said first and second moiety.

In a particularly preferred embodiment, the donor moiety and acceptor moiety form a fluorescence resonance energy transfer (FRET) pair. Molecular energy transfer (MET) is a process by which energy is passed non-radiatively between a donor molecule and an acceptor molecule. Fluorescence resonance energy transfer (FRET) is a form of MET. FRET arises from the properties of certain chemical compounds; when excited by exposure to particular wavelengths of light, they emit light (i.e., they fluoresce) at a different wavelength. Such compounds are termed fluorophores. In FRET, energy is passed non-radiatively over a long distance (10-100 Å) between a donor molecule, which is a fluorophore, and an acceptor molecule. The donor absorbs a photon and transfers this energy nonradiatively to the acceptor (Förster, 1949, Z. Naturforsch. A4: 321-327; Clegg, 1992, Methods Enzymol. 211: 353-388). When two fluorophores whose excitation and emission spectra overlap are in close proximity, excitation of one fluorophore will cause it to emit light at wavelengths that are absorbed by and that stimulate the second fluorophore, causing it in turn to fluoresce. In other words, the excited-state energy of the first (donor) fluorophore is transferred by a resonance induced dipole—dipole interaction to the neighbouring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher. Both quenchers and acceptors may be utilised in the present invention. Pairs of molecules that can engage in fluorescence resonance energy transfer (FRET) are termed FRET pairs. In order for energy transfer to occur, the donor and acceptor molecules must typically be in close proximity (up to 70 to 100 Å) (Clegg, 1992, Methods Enzymol. 211: 353-388; Selvin, 1995, Methods Enzymol. 246: 300-334). The efficiency of energy transfer falls off rapidly with the distance between the donor and acceptor molecules. According to Förster (1949, Z. Naturforsch. A4:321-327), the efficiency of energy transfer is proportional to $D \times 10^{-6}$, where D is the distance between the donor and acceptor. Effectively, this means that FRET can most efficiently occur up to distances of about 70 Å. Molecules that are commonly used in FRET are discussed in a separate section. Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

In one particularly preferred embodiment, said donor moiety is fluorescein or a derivative thereof, and said acceptor moiety is DABCYL. Preferably, the fluorescein derivative comprises, consists essentially of or consists of 6-carboxy fluorescein.

The MET labels can be attached at any suitable point in the primers. In a particularly preferred embodiment, the donor and acceptor moieties are positioned on complementary nucleotides within the stem loop structure, such that whilst the stem loop is intact, the moieties are in close physical proximity to one another. However, the primers of the invention may be labelled with the moieties in any position effective to allow MET/FRET between the respective donor and acceptor in the absence of amplification and separation of the donor and acceptor once the primer is incorporated into an amplification product.

The stem loop or hairpin structure sequence does not depend upon the nucleotide sequence of the target gene (gene of interest or reference gene) since it does not bind thereto. Accordingly, "universal" stem loop or hairpin sequences may be designed which can then be combined with a sequence specific primer to facilitate real-time detection of a sequence of interest. The main sequence requirement is that the sequence forms a stem loop/hairpin structure which is stable in the absence of amplification (and thus ensures efficient quenching). Thus, the sequence specific portion of the primer binds to a template strand and directs synthesis of the complementary strand. The primer therefore becomes part of the amplification product in the first round of amplification. When the complimentary strand is synthesised, amplification occurs through the stem loop/hairpin structure. This separates the fluorophore and quencher molecules, thus leading to generation of florescence as amplification proceeds.

The stem loop structure is preferably found at the 5' end of the sequence specific portion of the primer used in the amplification.

As mentioned above, this detector sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties.

As detailed in the experimental section, primers must be carefully selected in order to ensure sensitivity and specificity of the methods of the invention. Accordingly, particularly preferred primers for use in detecting methylation status of the gene include a primer comprising, consisting essentially of or consisting of the nucleotide sequence set forth as:

5'-AGCGATGCGTTCGAGCATCGCU-3' (SEQ ID NO: 1)

5'-ATTTTTGTTTGGAATTTAGGGTAG-3' (SEQ ID NO. 2)
and/or,

5'-AGCGATGCGTTCGAGCATCGCUCCAACATCAAACCATCACTCA-3' (SEQ ID NO. 3)
and/or,

5'-CCAACATCAAACCATCACTCA-3' (SEQ ID NO. 4)
and/or,

5'-TGGAATTTAGGGTAGTATTGT-3' (SEQ ID NO. 5)
and/or,

5'-AGCGATGCGTTCGAGCATCGCUTGGAATTTAGGGTAGTATTGT-3' (SEQ ID NO. 6)
and/or,

5'-CCCTCCACCAACATCAAA-3' (SEQ ID NO. 7)
and/or,

5'-TTAGGATGTGATGTTATTGATTTGT-3' (SEQ ID NO. 8)
and/or,

5'-AGCGATGCGTTCGAGCATCGCUTTAGGATGTGATGTTATTGATTTGT-3' (SEQ ID NO. 9)
and/or,

5'-TGTTTGGAATTTAGGGTAGTATTGT-3' (SEQ ID NO. 11)
and/or,

5'-AGCGATGCGTTCGAGCATCGCUTGTTTGGAATTTAGGGTAGTATTGT-3' (SEQ ID NO. 12)
and/or,

5'-CCATCACTCATTACTCAAAACAAA-3' (SEQ ID NO. 13)
and/or,

5'-ATTTTTGTTCGGAATTTAGGGTAG-3' (SEQ ID NO. 14)
and/or,

5'-AGCGATGCGTTCGAGCATCGCUCCGACGTCAAACCGTCGCTCG-3' (SEQ ID NO. 15)
and/or,

5'-CCGACGTCAAACCGTCGCTCG-3' (SEQ ID NO. 16)
and/or,

5'-CGGAATTTAGGGTAGTATCGT-3' (SEQ ID NO. 17)
and/or,

5'-AGCGATGCGTTCGAGCATCGCUCCCTCCGCCGACGTCAAA-3' (SEQ ID NO. 18)
and/or,

5'-CCCTCCGCCGACGTCAAA-3' (SEQ ID NO. 19)

SEQ ID NO 1 represents the sequence of the hairpin structure

SEQ ID NO 2, 5, 8, or 11 represent forward primer sequences complementary to the bisulfite converted unmethylated sequence of the Mage promoter SEQ ID NO 1 represents the hairpin structure sequence SEQ ID NO 6, 9 and 12 comprise the hairpin structure sequence and the sequence of SEQ ID NO. 5, 8 and 11 respectively.

SEQ ID NO. 4, 7 and 13, represent the reverse primer sequence complementary to the bisulfite converted unmethylated sequence of the Mage promoter.

SEQ ID NO 3 comprises the hairpin structure sequence and the sequence of SEQ ID NO. 4.

SEQ ID NO 14 and 17 represent forward primer sequences complementary to the bisulfite converted methylated sequence of the Mage promoter SEQ ID NO. 16 and 19, represent the reverse primer sequence complementary to the bisulfite converted methylated sequence of the Mage promoter.

SEQ ID NO 15 and 18 comprises the hairpin structure sequence and the sequence of SEQ ID NO. 16 and 19 respectively.

As detailed in the experimental section, expression and methylation levels of MAGE-A3 showed best concordance in the assays that incorporated SEQ ID NO. 2, 5 or 11, all three primers comprising the sequence 5' TGGAATTTAGGGTAG 3' (SEQ ID NO. 25). Thus in another embodiment, preferred primer binding to the promoter region of MAGE-A3 comprises SEQ ID NO. 25. The part of the primer complementary to the bisulfite converted sequence of the MAGE-A3 is preferably less than 25 bp; it is preferably 23, 22, 21, 20 or 19 bp in length. Thus the Mage-A3 specific part of such preferred primer is preferably between 24 and 18 bp, or between 23 and 19 bp in length. Preferably it is 19 bp in length. The primer may thus comprise any sequence of 23, 22, 21, 20 or 19 consecutive bases from the sequence 5'-ATTTTTGTTTGGAATTTAGGGTAGTATTGT-3' (SEQ ID NO. 26). The Mage-A3 specific part of the primer most preferably consists of the nucleotide sequence set forth as SEQ ID No. 2, 4, 5 or 7.

A primer comprising, consisting essentially of or consisting of the nucleotide sequence of any SEQ ID NO. 2, 3, 4, 5, 6, 7, 8, 9, 11, 12 or 13 is particularly useful for the detection of hypomethylated (unmethylated) MAGE-A3 gene. Preferred primers have the nucleotide sequence of SEQ ID NO. 2, 3, 4, 5, 6 or 7.

A primer comprising, consisting essentially of or consisting of the nucleotide sequence of any SEQ ID NO. 14, 15, 16, 17, 18 or 19 is particularly useful for the detection of hypermethylated (methylated) MAGE-A3 gene.

Preferred primer pairs for use in the methods/kits and assays of present invention comprise at least one primer comprising, consisting essentially of or consisting of the nucleotide sequence of any SEQ ID NO. 2, 3, 4, 5, 6, 7, 8, 9, 11, 12, 13, 14, 15, 16, 17, 18, 19 or 25. Preferred primer pairs comprise, consist essentially of or consist of the nucleotide sequence of any SEQ ID NO. 2 and 3; SEQ ID NO.6 and 7; SEQ ID NO. 9 and 4; SEQ ID NO. 12 and 13; SEQ ID NO. 14 and 15; or SEQ ID NO. 17 and 18. A most preferred primer pair comprises, consists essentially of or consists of the nucleotide sequence of SEQ ID NO.6 and 7.

Either one or both of the primers may be labelled with or synthesised to incorporate a suitable stem loop or hairpin structure carrying a donor and acceptor moiety, preferably at the 5' end, as discussed in detail above. In a preferred embodiment, one or both of the primer(s) is labelled with or synthesised to incorporate, preferably at the 5' end, the stem loop structure comprising, consisting essentially of or consisting of the nucleotide sequence set forth as

5'-AGCGATGCGTTCGAGCATCGCU-3'. (SEQ ID NO: 1)

This detector sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties. In a particularly preferred embodiment, the stem loop or hairpin structure, especially the nucleic acid comprising, consisting essentially of or consisting of the sequence set forth as SEQ ID NO: 1, is labelled at the 5'end with FAM and at the 3'end with DABCYL. Other preferred combinations are discussed herein, which discussion applies mutatis mutandis.

These primers form separate aspects of the present invention. Further characteristics of these primers are summarized in the detailed description (experimental part) below. It is noted that variants of these sequences may be utilised in the present invention. In particular, additional flanking sequences may be added, for example to improve binding specificity or the formation of a stem loop, as required. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences of the primers and/or probes set forth in SEQ ID NO:1 to 9 and 11 to 19 or 25. The primers and hairpin structures may incorporate synthetic nucleotide analogues as appropriate or may be DNA, RNA or PNA based for example, or mixtures thereof. Similarly alternative fluorescent donor and acceptor moieties/FRET pairs may be utilised as appropriate. In addition to being labelled with the fluorescent donor and acceptor moieties, the primers may include modified oligonucleotides and other appending groups and labels provided that the functionality as a primer and/or stem loop/hairpin structure in the methods of the invention is not compromised.

For each primer pair at least one primer is labelled with a donor and an acceptor moiety of a molecular energy transfer pair arranged such that in the absence of amplification, the acceptor moiety quenches fluorescence emitted by the donor moiety (upon excitation) and during amplification, the stem loop structure is disrupted so as to separate the donor and acceptor moieties sufficiently to produce a detectable fluorescence signal which is detected in real-time to provide an indication of the gene copy number of the gene. Preferably, said donor moiety and said acceptor moiety are a FRET pair. In one embodiment, said donor moiety and said acceptor moiety are selected from 5-carboxyfluorescein or 6-carboxyfluorescein (FAM), 2'7'-dimethoxy-4'5'-dichloro-6-carboxyfluorescein (JOE), rhodamine, 6-carboxyrhodamine (R6G), N,N,N'-tetramethyl-6-carboxyrhodamine (TAMRA), 6-carboxy-X-rhodamine (ROX), 5-(2'-aminoethyl)aminonapthalene-1-sulfonic acid (EDANS), anthranilamide, coumarin, terbium chelate derivatives, Malachite green, Reactive Red 4, DABCYL, tetramethyl rhodamine, pyrene butyrate, eosine nitrotyrosine, ethidium, and Texas Red. In a further embodiment, said donor moiety is selected from fluorescein, 5-carboxyfluorescein or 6-carboxyfluorescein (FAM), rhodamine, 5-(2'-aminoethyl)aminonapthalene-1-sulfonic acid (EDANS), anthranilamide, coumarin, terbium chelate derivatives, Malachite green, and Reactive Red 4, and said acceptor moiety is selected from DABCYL, rhodamine, tetramethyl rhodamine, pyrene butyrate, eosine nitrotyrosine, ethidium, and Texas Red. Preferably, said donor moiety is fluorescein or a derivative thereof, and said acceptor moiety is DABCYL and most preferably the donor moiety is 6-carboxyfluorescein. Other preferred combinations, particularly in a multiplexing context, are discussed herein and these combinations are also envisaged for these aspects of the invention.

The invention also provides kits which may be used in order to carry out the methods of the invention. The kits may incorporate any of the preferred features mentioned in connection with the various methods (and uses) of the invention described herein. Thus, the invention provides a kit for detecting the presence and/or amount of a methylated or unmethylated gene of interest in a DNA-containing sample, comprising at least one primer pair of the invention. Preferably, the kit incorporates a primer pair of the invention for detecting the presence and/or amount of unmethylated and/or methylated MAGE-A3 gene and a primer pair for detecting the presence and/or amount of a reference gene, in particular beta-actin. Thus, the kit may comprise primer pairs comprising a primer comprising, consisting essentially of or consisting of the nucleotide sequence set forth as SEQ ID NOs 2, 3, 4, 5, 6, 7, 8, 9, 11, 12, 13, 14, 15, 16, 17, 18, 19 or 25. Preferably, at least one primer in each primer pair is labelled with an appropriate stem loop or hairpin structure to facilitate detection in real-time, as discussed above (which discussion applies here mutatis mutandis). Most preferably at least one primer in each primer pair incorporates the stem loop or hairpin structure which comprises, consists essentially of or consists of the nucleotide sequence set forth as SEQ ID NO:1. The stem loop structure is labelled with an appropriate donor and acceptor moiety, as discussed herein (which discussion applies here mutatis mutandis).

As aforementioned, further characteristics of the primers of the invention are summarized in the detailed description (experimental part) below. Variants of these sequences may be utilised in the present invention as discussed herein. Alternative fluorescent donor and acceptor moieties/FRET pairs may be utilised as appropriate, as discussed herein.

In one embodiment, the kit of the invention further comprises a reagent which modifies unmethylated cytosine, as discussed herein (in preference to methylated cytosine residues which are protected). Such a reagent is useful for distinguishing methylated from unmethylated cytosine residues. In a preferred embodiment, the reagent comprises bisulphite, preferably sodium bisulphite. This reagent is capable of converting unmethylated cytosine residues to uracil, whereas methylated cytosines remain unconverted. This difference in residue may be utilised to distinguish between methylated and unmethylated nucleic acid in a downstream process, such as PCR using primers which distinguish between cytosine and uracil (cytosine pairs with guanine, whereas uracil pairs with adenine).

As discussed with respect to the methods of the invention herein, suitable controls may be utilised in order to act as quality control for the methods. Accordingly, in one embodiment, the kit of the invention further comprises, consists essentially of or consists of one or more control nucleic acid molecules of which the methylation status is known. These (one or more) control nucleic acid molecules may include both nucleic acids which are known to be, or treated so as to be, methylated and/or nucleic acid molecules which are known to be, or treated so as to be, unmethylated. One example of a suitable internal reference gene, which is generally unmethylated, but may be treated so as to be methylated, is beta-actin.

The kits of the invention may additionally include suitable buffers and other reagents for carrying out the claimed methods of the invention. Thus, the discussion provided in respect of the methods of the invention applies mutatis mutandis here and is not repeated for reasons of conciseness. In one embodiment, the kit of the invention further comprises, consists essentially of, or consists of nucleic acid amplification buffers.

The kit may also additionally comprise, consist essentially of or consist of enzymes to catalyze nucleic acid amplification. Thus, the kit may also additionally comprise, consist essentially of or consist of a suitable polymerase for nucleic acid amplification. Examples include those from both family A and family B type polymerases, such as Taq, Pfu, Vent etc.

The various components of the kit may be packaged separately in individual compartments or may, for example be stored together where appropriate.

The kit may also incorporate suitable instructions for use, which may be printed on a separate sheet or incorporated into the kit's packaging for example. The instructions may facilitate use of the kits of the invention with an appropriate real-time amplification apparatus, a number of which are commercially available.

The last step of the real-time methods of the invention involves quantifying the results of the real-time detection against a standard curve for the methylated or unmethylated gene of interest, and optionally the reference gene (where included). Standard curves may be generated using a set of standards. Each standard contains a known copy number, or concentration, of the gene of interest and/or reference gene as appropriate. Typically, a baseline value of fluorescence will be set to account for background fluorescence. For example, in one embodiment the Sequence Detection System (SDS) software is utilised. This software sets a default baseline range of cycles 3 to 15 of the amplification reaction before amplification products are detected. A threshold value of fluorescence is then defined at a statistically significant value above this baseline. Typically, the threshold is set to 10 standard deviations above the baseline fluorescence. Appropriate software is provided with apparatus for carrying out real-time amplification reactions. The software automatically calculates the baseline and threshold values for the reaction. The threshold cycle value (Ct) can then be determined for each standard. This is the number of cycles required to achieve the threshold amplification level. Thus, the greater the initial concentration of the gene standard in the reaction mixture, the fewer the number of cycles required to achieve a particular yield of amplified product. A plot of Ct against the $\log_{10}$ of the known initial copy number of the set of standard DNAs produces a straight line. This is the standard curve. Thus, the Ct value for the amplification of the gene of interest and reference gene, where utilised, can each be interpolated against the respective standard curve in order to determine the copy number in the DNA-containing sample. Thus, the output of the method is the gene copy number for each of the gene of interest and reference gene. The results may be normalised by dividing the gene copy number of the methylated or unmethylated gene of interest by the gene copy number of the reference gene. In a preferred embodiment, the Applied Biosystems 7900 HT fast real-time PCR system is used to carry out the methods of the invention. Preferably, SDS software is utilised, preferably including a suitable algorithm such as the Auto CT algorithm for automatically generating baseline and threshold values for individual detectors.

Whilst the methods of the invention may be utilised with any suitable amplification technique, it is most preferred that amplification is carried out using the polymerase chain reaction (PCR). Thus, whilst PCR is a preferred amplification method, to include variants on the basic technique such as nested PCR, equivalents may also be included within the scope of the invention. Examples include, without limitation, isothermal amplification techniques such as NASBA, 3SR, TMA and triamplification, all of which are well known in the art and suitable reagents are commercially available. Other suitable amplification methods include, without limitation, the ligase chain reaction (LCR) (Barringer et al, 1990), MLPA, selective amplification of target polynucleotide sequences (U.S. Pat. No. 6,410,276), consensus sequence primed polymerase chain reaction (U.S. Pat. No 4,437,975), invader technology (Third Wave Technologies, Madison, Wis.), strand displacement technology, arbitrarily primed polymerase chain reaction (WO90/06995) and nick displacement amplification (WO2004/067726).

The real-time PCR methods of the invention generally involve steps of lowering the temperature to allow primer annealing, raising the temperature for primer extension, raising the temperature for denaturation and lowering the temperature for data-collection. In one specific embodiment, the data-collection step is carried out at a temperature of between approximately 60° C. and 64° C., most preferably at approximately 62° C. since this has been shown to give maximally sensitive and specific results as discussed in Example section.

In a specific embodiment, the thermal profiling of the polymerase chain reaction comprises between 40 and 50 repeats, preferably approximately 45 repeats of the cycle:

(a) approximately 50° C. for approximately 2 minutes
(b) approximately 95° C. for approximately 10 minutes
(c) approximately 95° C. for approximately 15 seconds
(d) approximately 62° C. for approximately 1 minute The preferred reaction scheme shown to produce specific and sensitive results in the methods of the invention is Stage1: 50° C. for 2 min, Stage2: 95° C. for 10 min, Stage3: 95° C. for 15 sec, 59° C. for 30 sec, 59° C. for 30 sec (=plateau-data collection) for 45 repeats.

It is possible for the methods of the invention to be used in order to detect more than one gene of interest in the same reaction. Through the use of several specific sets of primers, amplification of several nucleic acid targets can be performed in the same reaction mixture. This may be termed "multiplexing". In a preferred embodiment, one or both primers for each target may be hairpin primers labeled with a fluorescent moiety and a quenching moiety that form a FRET pair. Amplification of several nucleic acid targets requires that a different fluorescent donor and/or acceptor moiety, with a different emission wavelength, be used to label each set of primers. During detection and analysis after an amplification, the reaction mixture is illuminated and read at each of the specific wavelengths characteristic for each of the sets of primers used in the reaction. It can thus be determined which specific target DNAs in the mixture were amplified and labelled. In a specific embodiment, two or more primer pairs for amplification of different respective target sequences are used. Thus the presence and/or amount of a panel of methylated/unmethylated genes of interest can be detected in a single DNA-containing sample Multiplexing can also be utilised in the context of detecting both the gene of interest and a reference gene in the same reaction. Again, primers labelled with appropriate distinguishable donor and/or acceptor moieties allow the signal generated by amplification of the gene of interest and reference gene respectively to be distinguished.

In one embodiment, a universal quencher is utilised together with suitable fluorophore donors each having a distinguishable emission wavelength maximum. A particularly preferred quencher is DABCYL. Together with DABCYL as quencher, the following fluorophores may each be utilised to allow multiplexing: Coumarin (emission maximum of 475 nm), EDANS (491 nm), fluorescein (515 nm), Lucifer yellow (523 nm), BODIPY (525 nm), Eosine (543 nm), tetramethylrhodamine (575 nm) and texas red (615 nm) (Tyagi et al., Nature Biotechnology, Vol. 16, January 1998; 49-53). Other preferred combinations are discussed herein.

In an alternative embodiment, the DNA-containing sample can be split and the methods of the invention carried out on suitable portions of the sample in order to obtain directly comparable results. Thus, where both the gene of interest and a reference gene are detected, the sample may be split two ways to allow detection of amplification of the gene of interest in real time in one sample portion and detection of amplification of the reference gene in real time in the other sample portion. The sample may be split further to allow suitable control reactions to be carried out, as required. The benefit of this scheme is that a universal FRET pair can be used to label each primer pair and removes the requirement to detect emission at a range of wavelengths. However, this method does rely upon obtaining a suitable sample initially to permit dividing the sample. Whilst any suitable reaction volume may be utilised, in one specific embodiment, the total reaction volume for the amplification step is between approximately 10 and 40 µl, more preferably between approximately 10 and 30 µl and most preferably around 12 µl In one aspect, the oligonucleotides, primers or probes, primer pairs, kits or methods of the present invention are used for diagnosing cancer or predisposition of cancer, wherein the presence of unmethylated (or hypomethylated) MAGE-A3 in the sample is indicative for cancer or predisposition to cancer. Thus, the present invention provides kits, methods and primers for diagnosing cancer or predisposition to cancer.

"Diagnosis" is defined herein to include screening for a disease or pre-stadia of a disease, identifying a disease or prestadia of a disease, monitoring staging and the state and progression of the disease, checking for recurrence of disease following treatment and monitoring the success of a particular treatment. The tests may also have prognostic value, and this is included within the definition of the term "diagnosis". The prognostic value of the tests may be used as a marker of potential susceptibility to cancer or as a marker for progression to cancer. Thus patients at risk may be identified before the disease has a chance to manifest itself in terms of symptoms identifiable in the patient. In a preferred embodiment, the cancer is selected from lung cancer, melanoma or bladder cancer. In a preferred embodiment, the methods and assays for diagnosis use at least one oligonucleotide comprising, consisting, consisting essentially of, or consisting of the nucleotide sequence of any SEQ ID NO. 2, 3, 4, 5, 6, 7, 8, 9, 11, 12, 13, 14, 15, 16, 17, 18, 19 or 25. In a preferred embodiment, diagnosis of cancer or predisposition to cancer uses oligonucleotides comprising, consisting, consisting essentially of, or consisting of the nucleotide sequence of any SEQ ID NO. 2, 3, 4, 5, 6, 7, 8, 9, 11, 12, 13, or 25 and detects the unmethylated form of the gene. In an alternative embodiment, the methods and assays for diagnosis use at least one oligonucleotide comprising, consisting essentially of, or consisting of the nucleotide sequence of any SEQ ID NO. 14, 16, 17 or 19.

Testing can be performed diagnostically or in conjunction with a therapeutic regimen. As mentioned above, RT-PCR assays that establish the predictive value of MAGE-A3 expression in NSCLC have been described. These assays find their application in the selection of patients suitable for treatment with a MAGE-A3 immunotherapeutic. The inventors have shown that an assay designed for the detection of unmethylated MAGE-A3 employing oligonucleotides, primers or probes, primer pairs or kits of the invention, can reliably categorize samples as MAGE-A3 expressing. The methylation status result obtained with the methylation test is in good concordance with the results obtained with an existing RT-PCR test for MAGE-A3 detection that is used on RNA samples. Accordingly, the methylation test has clinical application.

In a further aspect the invention provides a method of predicting the likelihood of successful treatment of cancer in a subject comprising:

(a) contacting/treating a DNA-containing test sample obtained from a subject with a reagent which selectively modifies unmethylated cytosine residues in the DNA to produce detectable modified residues but which does not modify methylated cytosine residues (b) amplifying at least a portion of the unmethylated MAGE A3 gene using at least one primer pair, at least one primer of which is designed to bind only to the sequence of unmethylated DNA respectively following treatment with the reagent, wherein at least one primer in the primer pair comprises, consists essentially of, or consists of the nucleotide sequence of any of SEQ ID NO. 2, 3, 4, 5, 6, 7, 8, 9, 11, 12, 13 or 25

(c) determining the methylation status of the MAGE-A3 gene;

wherein the presence of unmethylated MAGE-A3 in the sample indicates that the likelihood of successful treatment with a MAGE-A3 immunotherapeutic is higher than if no or lower levels of unmethylated MAGE-A3 gene is detected.

Step (c) involves identifying whether an amplification product has formed. The identification of the amplification product (using any suitable technique as discussed herein) indicates the present of unmethylated or hypomethylated MAGEA3 in the sample.

Of course, the reverse situation is also applicable and so the methods of the invention may likewise be utilised in order to determine whether there is likely to be resistance to, or unsuccessful treatment using, an MAGEA3 immunotherapeutic agent—the absence of unmethylated MAGE-A3 in the sample indicates there is likely to be resistance to treatment and/or that treatment is likely to be unsuccessful. Primers specific for methylated DNA may also be employed in complementary methods, in certain embodiments.

The methods of the invention may also be utilised to select a suitable course of treatment for a patient—the presence of unmethylated MAGE-A3 indicates that MAGE-A3 immunotherapeutic agents may be beneficially administered, whereas the absence or low level of unmethylated MAGE-A3 indicates that immunothereapeutic agents are contra-indicated. The discussion provided in respect of the oligonucleotides, primers or probes, primer pairs, kits or methods of the invention applies to the present aspect mutatis mutandis and all embodiments are therefore envisaged, as appropriate, for this aspect of the invention.

By "likelihood of successful treatment" is meant the probability that treatment of the cancer using any one or more of the listed therapeutic agents, preferably a MAGE-A3 immunotherapeutic or a composition comprising MAGE-A3, will be successful.

"Resistance" is defined as a reduced probability that treatment of cancer will be successful using any one of the specified immunotherapeutic agents and/or that higher dose will be required to achieve a therapeutic effect.

Hypomethylation of MageA3 may be linked to certain cancer types. Accordingly, in a specific embodiment, the invention provides a method of detecting a predisposition to, or the incidence of, bladder cancer, lung cancer, including NSCLC or melanoma in a sample comprising detecting the methylation status of the MAGE-A3 gene using the oligonucleotides, primers or probes, primer pairs, kits or methods of the invention, wherein detection of unmethylated MAGE-A3 in the sample is indicative of a predisposition to, or the incidence of, cancer and in particular melanoma; lung cancer including non-small cell lung carcinoma (NSCLC); or bladder cancer, including transitional cell carcinoma. In a further embodiment, the tumour or cancer is selected from breast cancer; head and neck cancer including oesophagus carcinoma; squamous cell carcinoma; seminoma; liver cancer; multiple myeloma and colon carcinoma.

In a further aspect, there is provided a method for determining the presence of a MAGE-A3 positive tumor comprising detecting the methylation status of the MAGE-A3 gene in a sample with use of the oligonucleotides, primers or probes, primer pairs, kits or methods described herein, wherein the presence of unmethylated MAGE-A3 is indicative for the presence of a MAGE-A3 positive tumor.

Testing can be performed diagnostically or in conjunction with a therapeutic regimen. MAGE-A3 specific immunotherapeutics (ASCI) have been developed and are currently being evaluated in clinical trials. Testing can also be used to determine what therapeutic or preventive regimen to employ on a patient and be used to monitor efficacy of a therapeutic regimen.

Accordingly, the invention further provides a method for identifying and/or selecting a patient suitable for treatment with a MAGE-A3 immunotherapeutic comprising detecting the methylation status of the MAGE-A3 gene in a sample of the patient with use of the oligonucleotides, primers or probes, primer pairs, kits or methods described herein, wherein if the MAGE-A3 gene is unmethylated the subject is identified and/or selected for treatment with the MAGE-A3 immunotherapeutic.

Alternatively, if the gene is not unmethylated the subject is preferably not selected for treatment with a MAGE-A3 immunotherapeutic.

In a related aspect, the invention provides a method for predicting the likelihood of successful treatment of cancer comprising detecting the methylation status of the MAGE-A3 gene in a sample of the patient with use of the oligonucleotides, primers or probes, primer pairs, kits or methods described herein, wherein if the gene is unmethylated the likelihood of successful treatment with a MAGE-A3 immunotherapeutic is higher than if the gene is methylated.

Alternatively, the absence of unmethylated MAGE-A3 in the sample indicates that the likelihood of resistance to treatment with a MAGE-A3 immunotherapeutic is higher than if the gene is unmethylated. Thus, the detection of a methylated MAGE-A3 gene (or lack of detection of the hypomethylated gene) indicates that the probability of successful treatment with an immunotherapeutic is low.

Thus, the patient population may be selected for treatment on the basis of their methylation status with respect to the MAGE-A3 gene. This leads to a much more focussed and personalised form of medicine and thus leads to improved success rates since patients will be treated with drugs which are most likely to be effective.

In a further related aspect, the invention provides a method of selecting a suitable treatment regimen for cancer comprising detecting the methylation status of the MAGE-A3 gene in a sample of the patient with use of the oligonucleotides, primers or probes, primer pairs, kits or methods described herein, wherein if the gene is unmethylated, an immunotherapeutic (in particular a MAGE immunotherapeutic) is selected for treatment.

Alternatively, if the gene is not unmethylated, treatment with an immunotherapeutic is contra-indicated.

Also provided is a method of treating cancer in a subject comprising administration of an immunotherapeutic, wherein the subject has been selected for treatment on the basis of measuring the methylation status of a MAGE-A3 gene, according to any of the methods of the invention or by using an oligonucleotide, primer or probe, primer pair, kit or a method as described herein. Preferably, for all of the different aspects described herein, the detection of unmethylated MAGE-A3 gene corresponds to an increased level of MAGE-A3 protein.

MAGE-A3 immunotherapeutics, useful in the present invention, include MAGE-A3 based compositions. Examples of compositions comprising MAGE-A3 include compositions comprising full length MAGE-A3, substantially full-length MAGE-A3 and fragments of MAGE-A3, for example peptides of MAGE-A3.

Examples of peptides that may be used in the present invention include the following MAGE-A3 peptides:

| SEQ ID NO | Peptide sequence |
|---|---|
| SEQ ID NO: 27 | FLWGPRALV |
| SEQ ID NO: 28 | EVDPIGHLY |
| SEQ ID NO: 29 | MEVDPIGHLY |
| SEQ ID NO: 30 | VHFLLLKYRA |
| SEQ ID NO: 31 | LVHFLLLKYR |
| SEQ ID NO: 32 | LKYRAREPVT |
| SEQ ID NO: 33 | ACYEFLWGPRALVETS |
| SEQ ID NO: 34 | TQHFVQENYLEY |

The MAGE protein may be full length MAGE-A3 or may comprise a substantially full-length fragment of MAGE3, for example amino acids 3-314 of MAGE3 (312 amino acids in total), or other MAGE-A3 fragments in which between 1 and 10 amino acids are deleted from the N-terminus and/or C-terminus of the MAGE-A3 protein.

In one embodiment, the MAGE-A3 protein, fragment or peptide may be linked to a fusion partner protein.

The MAGE-A3 protein, fragment or peptide and fusion partner protein may be chemically conjugated, or may be expressed as a recombinant fusion protein. In an embodiment in which the antigen and partner are expressed as a recombinant fusion protein, this may allow increased levels to be produced in an expression system compared to non-fused protein. Thus the fusion partner protein may assist in providing T helper epitopes (immunological fusion partner protein), preferably T helper epitopes recognised by humans, and/or assist in expressing the protein (expression enhancer protein) at higher yields than the native recombinant protein. In one embodiment, the fusion partner protein may be both an immunological fusion partner protein and expression enhancing partner protein.

In one embodiment of the invention, the immunological fusion partner protein that may be used is derived from protein D, a surface protein of the gram-negative bacterium, *Haemophilus influenza* B (WO 91/18926) or a derivative thereof. The protein D derivative may comprise the first ⅓ of the protein, or approximately the first ⅓ of the protein. In one embodiment, the first N-terminal 109 residues of protein D may be used as a fusion partner to provide a MAGE-A3 antigen with additional exogenous T-cell epitopes and increase expression level in *E. coli* (thus acting also as an expression enhancer). In an alternative embodiment, the protein D derivative may comprise the first N-terminal 100-110 amino acids or approximately the first N-terminal 100-110 amino acids. In one embodiment, the protein D or derivative thereof may be lipidated and lipoprotein D may be used: the lipid tail may ensure optimal presentation of the antigen to antigen presenting cells. In an alternative embodiment, the protein D or derivative thereof is not lipidated. The "secretion sequence" or "signal sequence" of protein D, refers to approximately amino acids 1 to 16, 17, 18 or 19 of the naturally occurring protein. In one embodiment, the secretion or signal sequence of protein D refers to the N-terminal 19 amino acids of protein D. In one embodiment, the secretion or signal sequence is included at the N-terminus of the protein D fusion partner. As used herein, the "first third (⅓)", "first 109 amino acids" and "first N-terminal 100-110 amino acids" refer to the amino acids of the protein D sequence immediately following the secretion or signal sequence. Amino acids 2-K and 3-L of the signal sequence may optionally be substituted with the amino acids 2-M and 3-D.

In one embodiment, the MAGE-A3 may be Protein D-MAGE-A3-His, a 432-amino-acid-residue fusion protein. This fusion protein comprises the signal sequence of protein D, amino acids 1 to 109 of Protein D, 312 amino acids from the MAGE-A3 protein (amino acids 3-314), a spacer and a polyhistidine tail (His) that may facilitate the purification of the fusion protein during the production process, for example:

i) An 18-residue signal sequence and the first N-terminal 109 residues of protein D;
ii) Two unrelated residues (methionine and aspartic acid);
iii) Residues 3-314 of the native MAGE-3 protein;
iv) Two glycine residues functioning as a hinge region; and
v) seven Histidine residues.

The amino acid sequence for this molecule is shown in FIG. 10 (SEQ ID NO: 40). This antigen and those summarised below are described in more detail in WO 99/40188.

In another embodiment the immunological fusion partner protein may be the protein known as LytA or a protein derived therefrom. LytA is derived from *Streptococcus pneumoniae* which synthesise an N-acetyl-L-alanine amidase, amidase LytA, (coded by the LytA gene (Gene, 43 (1986) page 265-272)) an autolysin that specifically degrades certain bonds in the peptidoglycan backbone. The C-terminal domain of the LytA protein is responsible for the affinity to choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described (Biotechnology: 10, (1992) page 795-798). In one embodiment, the C terminal portion of the molecule may be used. The repeat portion of the LytA molecule found in the C terminal end starting at residue 178 may be utilised. In one embodiment, the LytA portion may incorporate residues 188-305.

Other fusion partners include the non-structural protein from influenzae virus, NS1 (hemagglutinin). In one embodiment, the N terminal 81 amino acids of NS1 are utilised, although different fragments may be used provided they include T-helper epitopes.

In one embodiment of the present invention, the MAGE-A3 protein may comprise a derivatised free thiol. Such antigens have been described in WO99/40188. In particular carboxyamidated or carboxymethylated derivatives may be used.

In a further embodiment the MAGE-A3 composition comprises a nucleic acid molecule encoding a MAGE-A3 protein, fragment or peptide or fusion protein as described herein. In one embodiment of the present invention, the sequences may be inserted into a suitable expression vector and used for DNA/RNA vaccination. Microbial vectors expressing the nucleic acid may also be used as vector-delivered immunotherapeutics.

Examples of suitable viral vectors include retroviral, lentiviral, adenoviral, adeno-associated viral, herpes viral including herpes simplex viral, alpha-viral, pox viral such as Canarypox and vaccinia-viral based systems. Gene transfer techniques using these viruses are known to those skilled in the art. Retrovirus vectors for example may be used to stably integrate the polynucleotide of the invention into the host genome, although such recombination is not preferred. Replication-defective adenovirus vectors by contrast remain episomal and therefore allow transient expression. Vectors capable of driving expression in insect cells (for example baculovirus vectors), in human cells, yeast or in bacteria may be employed in order to produce quantities of the MAGE-A3 protein encoded by the polynucleotides of the present invention, for example for use as subunit vaccines or in immunoassays.

In a preferred embodiment the adenovirus used as a live vector is a replication defective simian adenovirus. Typically these viruses contain an E1 deletion and can be grown on cell lines that are transformed with an E1 gene. Preferred Simian adenoviruses are viruses isolated from Chimpanzee. In particular C68 (also known as Pan 9) (See U.S. Pat. No. 6,083, 716) and Pan 5, 6 and Pan 7 (WO 03/046124) are preferred for use in the present invention. These vectors can be manipulated to insert a heterologous gene of the invention such that the gene product may be expressed. The use, formulation and manufacture of such recombinant adenoviral vectors is set forth in detail in WO 03/046142.

Conventional recombinant techniques for obtaining nucleic acid sequences, and production of expression vectors are described in Maniatis et al., Molecular Cloning—A Laboratory Manual; Cold Spring Harbor, 1982-1989.

For protein based compositions, the proteins of the present invention may be provided either soluble in a liquid form or in a lyophilised form.

Each human dose may comprise 1 to 1000 µg of protein. In one embodiment, the dose may comprise 30-300 µg of protein.

The MAGE-A3 containing composition as described herein may further comprise a vaccine adjuvant, and/or an immunostimulatory cytokine or chemokine.

Suitable vaccine adjuvants for use in the present invention are commercially available such as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatised polysaccharides; polyphosphazenes; biodegradable microspheres; monophosphoryl lipid A and quil A. Cytokines, such as GM-CSF or interleukin-2, -7, or -12, and chemokines may also be used as adjuvants.

In one embodiment, the adjuvant may comprise a combination of monophosphoryl lipid A, such as 3-de-O-acylated monophosphoryl lipid A (3D-MPL) together with an aluminium salt. Alternatively, the adjuvant may comprise 3D-MPL or other toll like receptor 4 (TLR4) ligands such as aminoalkyl glucosaminide phosphates as disclosed in WO 98/50399, WO 01/34617 and WO 03/065806.

Another adjuvant that may be used is a saponin, for example QS21 (Aquila Biopharmaceuticals Inc., Framingham, Mass.), that may be used alone or in combination with other adjuvants. For example, in one embodiment, there is provided a combination of a monophosphoryl lipid A and saponin derivative, such as the combination of QS21 and 3D-MPL as described in WO 94/00153, or a composition in which the QS21 is quenched with cholesterol, as described in WO 96/33739. Other suitable formulations comprise an oil-in-water emulsion and tocopherol. In one embodiment, the adjuvant comprises QS21, 3D-MPL and tocopherol in an oil-in-water emulsion, as described in WO 95/17210.

Other adjuvants for use in the present invention may comprise TLR9 antagonists such as unmethylated CpG containing oligonucleotides, in which the CpG dinucleotide is unmethylated. Such oligonucleotides are well known and are described in, for example WO 96/02555.

Suitable oligonucleotides for use in the present invention (in this context) may include:

```
SEQ ID    TCC ATG ACG TTC CTG ACG TT       CpG 1826
NO: 35

SEQ ID    TCT CCC AGC GTG CGC CAT          CpG 1758
NO: 36

SEQ ID    ACC GAT GAC GTC GCC GGT GAC GGC
NO: 37    ACC ACG

SEQ ID    TCG TCG TTT TGT CGT TTT GTC GTT  CpG 2006,
NO: 38                                     CpG 7909

SEQ ID    TCC ATG ACG TTC CTG ATG CT       CpG 1668
NO: 39
```

CpG-containing oligonucleotides may also be used alone or in combination with other adjuvants. For example, in one embodiment, the adjuvant comprises a combination of a CpG-containing oligonucleotide and a saponin derivative particularly the combination of CpG and QS21 as disclosed in WO 00/09159 and WO 00/62800.

Accordingly there is provided a composition comprising MAGE-A3 as described herein, wherein the adjuvant comprises one or more of 3D-MPL, QS21, a CpG oligonucleotide, a polyethylene ether or ester or a combination of two or more of these adjuvants. The MAGE-A3 component within the composition may be presented in an oil in water or a water in oil emulsion vehicle or in a liposomal formulation, in certain embodiments.

In one embodiment, the adjuvant may comprise one or more of 3D-MPL, 021 and an immunostimulatory CpG oligonucleotide. In an embodiment all three adjuvant components are present. The components may be either presented in a liposomal formulation or an oil in water emulsion, such as described in WO 95/17210.

In another embodiment 3D MPL- and Qs21 are presented in an oil in water emulsion, and in the absence of a CpG oligonucleotide.

The amount of 3D-MPL used is generally small, but depending on the formulation may be in the region of 1-1000 µg per dose, preferably 1-500 µg per dose, and more preferably between 1 to 100 µg per dose.

The amount of CpG or immunostimulatory oligonucleotides in the adjuvants of the present invention is generally small, but depending on the formulation may be in the region of 1-1000 µg per dose, preferably 1-500 µg per dose, and more preferably between 1 to 100 µg per dose.

The amount of saponin for use in the adjuvants of the present invention may be in the region of 1-1000 µg per dose, preferably 1-500 µg per dose, more preferably 1-250 µg per dose, and most preferably between 1 to 100 µg per dose.

The adjuvant formulations as described herein may additionally comprise an oil in water emulsion and/or tocopherol or may be formulated in a liposomal composition.

Other suitable adjuvants include Montanide ISA 720 (Seppic, France), SAF (Chiron, Calif., United States), ISCOMS (CSL), MF-59 (Chiron), Ribi Detox, RC-529 (GSK, Hamilton, Mont.) and other aminoalkyl glucosaminide 4-phosphates (AGPs).

Generally, each human dose may comprise 0.1-1000 µg of antigen, for example 0.1-500 µg, 0.1-100 µg, or 0.1 to 50 µg. An optimal amount for a particular immunotherapeutic can be ascertained by standard studies involving observation of appropriate immune responses in vaccinated subjects. Following an initial vaccination, subjects may receive one or several booster immunisation adequately spaced.

Alternatively, a composition for use in the method of the present invention may comprise a pharmaceutical composition comprising MAGE-A3 as described herein in a pharmaceutically acceptable excipient.

The invention will now be described with respect to the following non-limiting examples:

BRIEF DESCRIPTION OF THE FIGURES

FIG. 1: Location of the MAGEA3_U primers on the non converted sequence (FIG. 1a—SEQ ID NO: 10) and corresponding converted sequence (FIG. 1b—SEQ ID NO: 41). MAGEA3_GO1 U primer position is boxed, MAGEA3_GO2 U primer position is highlighted, MAGEA3_FURUTA U primer postion is in bold, MAGEA3_QIU U primer position is underlined, The G position indicated by ▌ corresponds to the transcription start site.

FIG. 2: Location of the MAGEA3_GO_2_U primers on the non converted sequence (FIG. 2a—SEQ ID NO: 10) and corresponding converted sequence (FIG. 2b—SEQ ID NO: 41), underlined starts at the transcription start site.

FIG. 3: Limit of detection graph.

FIG. 6: MAGE-A3 methylation status in melanoma samples: Receiver Operating Characteristics (ROC) curves were calculated for the 4 MAGE-A3 Unmethylated assays by plotting the true positive rate (sensitivity) in function of the false positive rate (100-specificity).

FIG. 6e: Summary table of results obtained for each of the four assays.

FIG. 7: MAGE-A3 methylation status in lung biopsies: Receiver Operating Characteristics (ROC) curves were calculated for the 4 MAGE-A3 Unmethylated assays by plotting the true positive rate (sensitivity) in function of the false positive rate (100-specificity).

FIG. 7e: Summary table of results obtained for each of the four assays on lung biopsies.

FIG. 8: MAGE-A3 methylation status in lung FFPE samples: Receiver Operating Characteristics (ROC) curves were calculated for the 4 MAGE-A3 Unmethylated assays by plotting the true positive rate (sensitivity) in function of the false positive rate (100-specificity).

FIG. 8e: Summary table of results obtained for each of the four assays on lung FFPE samples.

FIG. 9: Effect of melanin on PCR inhibition when spiked at different steps of the reaction process

FIG. 10: Protein D-MAGE-A3-His SINGLE UNDERLINED=first 109 amino acids of Protein D DOUBLE UNDERLINED=Protein D signal sequence (18 aa)

Boxed =inserted/substituted sequences: Met-Asp at 2-3 (substituted); Met-Asp at 128-129(inserted) and Gly-Gly at 442-443 (inserted)

Bold=fragment of MAGE3: amino acids 3-314 of MAGE3 (312 AA total)

Grey=7 his tail

DETAILED DESCRIPTION—EXPERIMENTAL SECTION

Example 1

Real Time Amplifluor Assay

Figure 4:
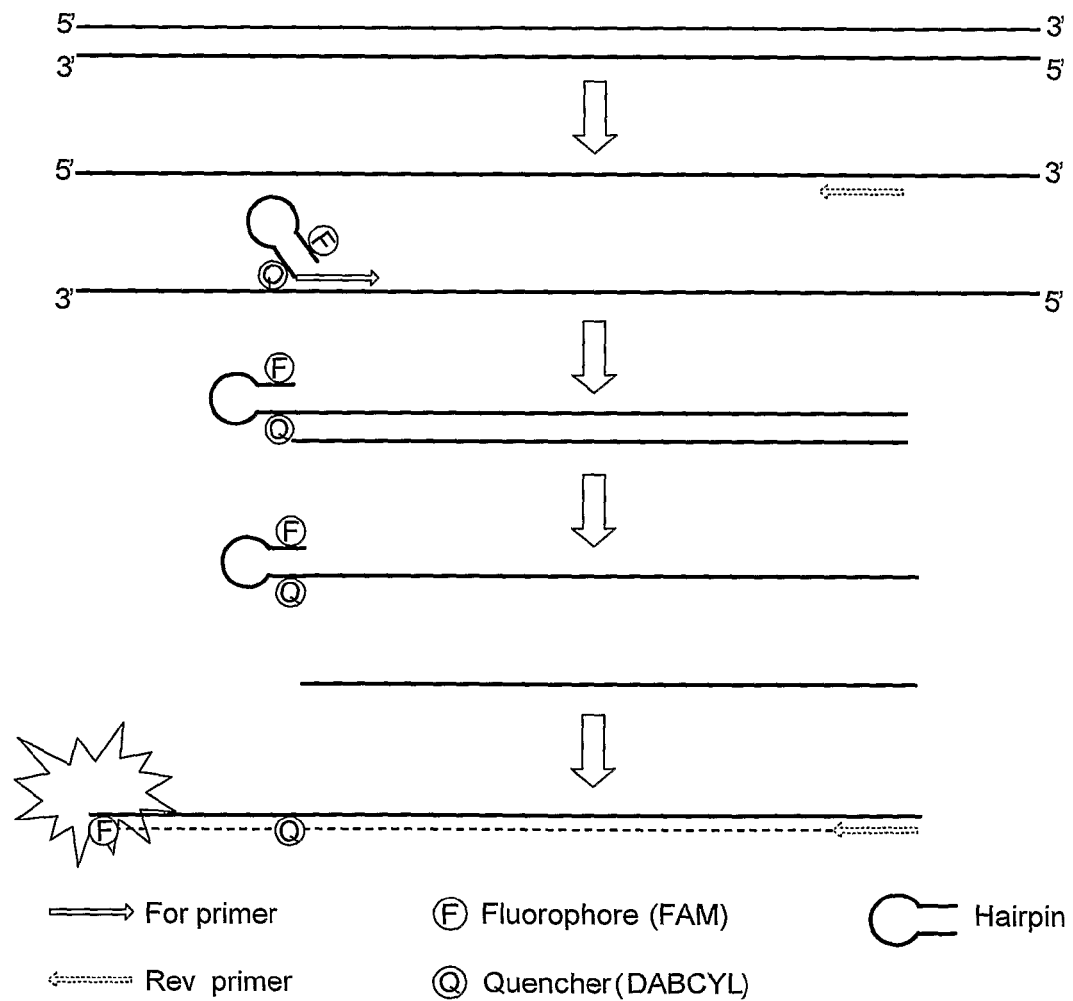
FIG. 4: Schematic overview of the Amplifluor® technique. At least one primer (forward primer in this case) in the primer pair contains a "hairpin" structure carrying a donor (FAM) and an acceptor moiety (DABCYL) of a molecular energy transfer pair. In the absence of amplification, fluorescence emitted by the donor moiety is effectively accepted by the acceptor moiety leading to quenching of fluorescence. During amplification, the primer is incorporated into an amplification product. During the second round of amplification the stem loop or hairpin structure is disrupted. The acceptor moiety is no longer capable of effectively quenching the fluorescence emitted by the donor moiety. Thus, the donor moiety produces a detectable fluorescence signal.

A direct real-time fluorescence based methylation-specific PCR assay (real-time MSP assay) was developed to define the methylation status of the MGMT promoter (Vlassenbroeck et al., J Mol Diagn 2008, 10:332-337). This technology is illustrated and summarised in the figure legend for FIG. 4 on page 70.

Analyte quantitations for Mage-A3 were successfully performed using this technology. This consisted of parallel amplification/quantification processes using specific primer and primer/detector pairs for Mage-A3 using the Amplifluor® assay format on an ABI Prism® 7900HT instrument (Applied Biosystems).

The final primer concentrations in the reaction mix were 100 nM for both forward primer/detector and reverse primer. 12.5 µl of iTaq™ Supermix with Rox (BioRad, 2× buffer) were used per PCR reaction. The total volume per reaction, including 5 µl of modified template DNA, was 25 µl. The ABI 7900HT SDS instrument was started 10 min before use, allowing the heated cover to reach 105° C. The following thermal profile was used: Stage1: 50° C. for 2 min, Stage2: 95° C. for 10 min, Stage3: 95° C. for 15 sec, 62° C. for 1 min (=plateau-data collection) for 45 repeats.

Plasmid material, used as standard curve was generated as follows: the promoter sequence as defined by the primers is PCR amplified and cloned (using suitable isolated and bisulphite modified cell line DNA). The sequence is verified by sequencing and compared to the published promoter sequence.

A standard curve ($2\times10^6$—20 copies) was included to determine copy numbers of unknown samples by interpolation of their Ct values to the standard curve. B-Actin was used as a reference gene in the assay.

Example 2

MAGE-A3 Assays and Primers Design

Primers useful for detecting unmethylated MAGE-A3 as described in Qiu et al.: Clinical Biochemistry 39 (2006), 259-2; Jang et al.: Cancer Research 61 (2001), 7959-7963 and Furuta et al.: Cancer Sci 95 (2004), 962-968 were synthesised, and are shown in Table 1 in addition to novel primer sequences.

In silico design of forward (F) and reverse (R) primers for detecting unmethylated or alternatively methylated form of Mage A3 were done using Primer3 software adapted to MSP requirements (http://fokker.wi.mit.edu/primer3/input.htm). Conditions were as follows: amplicon size: 60-120 nt; primer size: 18-27 nt; melting temp: 55-65° C.; max 3' self complementarity=0; Window of 200 bp around TSS (number to return=2000).

The U_primers were designed for detecting unmethylated Mage-A3 whereas the M_primers were designed for detecting methylated Mage-A3. Finally, primers A MAGE_A3 and MAGEA3_GO_1_U_F, MAGEA3_GO_2_U_R, MAGEA3_GO_1_U_R_AMP, MAGEA3_GO_2_U_F_AMP, MAGEA3_GO_1_M_F, MAGEA3_GO_2_M_F, MAGEA3_GO_1_M_R_AMP and MAGEA3_GO_2_M_R_AMP were retained for further investigation. Location of the U-primers relative to the Transcription Start Site (TSS) is shown in FIG. 1 and FIG. 2. The primers are positioned around the Transcription Start Site.

Either the forward or reverse primer was synthesised to incorporate a suitable stem loop or hairpin structure carrying a donor and acceptor moiety at the 5' end having the nucleotide sequence: 5'AGCGATGCGTTCGAGCATCGCU 3' (SEQ ID NO 1.)

Different MAGEA3 primer combinations were tested. Finally 4 U-assays and 2 M-assays were retained for further development. The selected primer combinations for each assay are summarized in Table 1.

TABLE 1

Primer and amplifluor detector sequences MAGEA3

| Name | Assay - Amplicon length | 5' to 3' Sequences Detector Modifications: 5' FAM and internal dUdabcyl |
|---|---|---|
| MAGEA3_GO_1_U_F Forward primer | U assay (set 2) - 142 bp | ATTTTTGTTCGGAATTTAGGGTAG (SEQ ID NO. 2) |
| MAGEA3_GO_1_U_R_AMP Reverse detector | | AGCGATGCGTTCGAGCATCGCUCCAACATCAAACC ATCACTCA (SEQ ID NO. 3) |
| MAGEA3_GO_2_U_F_AMP Forward detector | U assay (set 3) - 140 bp | AGCGATGCGTTCGAGCATCGCUTGGAATTTAGGGT AGTATTGT (SEQ ID NO. 6) |
| MAGEA3_GO_2_U_R Reverse primer | | CCCTCCACCAACATCAAA (SEQ ID NO. 7) |
| MAGEA3_FURUTA_U_F_AMP Forward detector | U assay (set 7) - 110 bp | AGCGATGCGTTCGAGCATCGCUTTAGGATGTGATG TTATTGATTTGT (SEQ ID NO. 9) |
| MAGEA3_FURUTA_U_R Reverse primer | | CCAACATCAAACCATCACTCA (SEQ ID NO. 4) |
| MAGEA3_QIU_U_F_AMP Forward detector | U assay (set 9) - 126 bp | AGCGATGCGTTCGAGCATCGCUTGTTTGGAATTTA GGGTAGTATTGT (SEQ ID NO. 12) |
| MAGEA3_QIU_U_R Reverse primer | | CCATCACTCATTACTCAAAACAAA (SEQ ID NO. 13) |
| ACTB_F_AMP Forward detector | Reference - 125 bp | AGCGATGCGTTCGAGCATCGCUTAGGGAGTATATA GGTTGGGGAAGTT (SEQ ID NO. 21, or SEQ ID NO: 1 + SEQ ID NO: 20) |
| ACTB_R Reverse primer | | AACACACAATAACAAACACAAATTCAC (SEQ ID NO. 22) |
| MAGEA3_GO_1_M_F Forward primer | M assay (set 2) - 142 bp | ATTTTTGTTCGGAATTTAGGGTAG (SEQ ID NO. 14) |
| MAGEA3_GO_1_M_R_AMP Reverse detector | | AGCGATGCGTTCGAGCATCGCUCCGACGTCAAACC GTCGCTCG (SEQ ID NO. 15) |
| MAGEA3_GO_2_M_F Forward primer | M assay (set 4) - 140 bp | CGGAATTTAGGGTAGTATCGT (SEQ ID NO. 17) |
| MAGEA3_GO_2_M_R_AMP Reverse detector | | AGCGATGCGTTCGAGCATCGCUCCCTCCGCCGACG TCAAA (SEQ ID NO. 18) |

Example 3

Analytical Assay Performance

The analytical performance (detection limit and specificity) of the assay was demonstrated using reconstructed substrates.

Limit of Detection

To determine the sensitivity of MSP for the unmethylated pattern, positive confirmed cell line material (LNCaP and Gerl), was serially diluted and mixed with control (negative) cell line DNA (DU145). Dilutions of $\frac{1}{10}$; $\frac{1}{100}$ and $\frac{1}{500}$ were made (see Table 2). A total amount of 750 ng of DNA (U DNA+M DNA) was bisulphite treated using the EZ DNA Methylation kit from Zymo Research.

TABLE 2

| Dilution scheme cell mixtures | |
|---|---|
| U DNA (ng) [LNCaP or Gerl] | M DNA (ng) [DU145] |
| 750 ng | 0 ng |
| 75 ng | 675 ng |
| 7.5 ng | 742.5 ng |
| 1.5 ng | 748.5 ng |
| 0 ng | 750 ng |

Figure 3A:
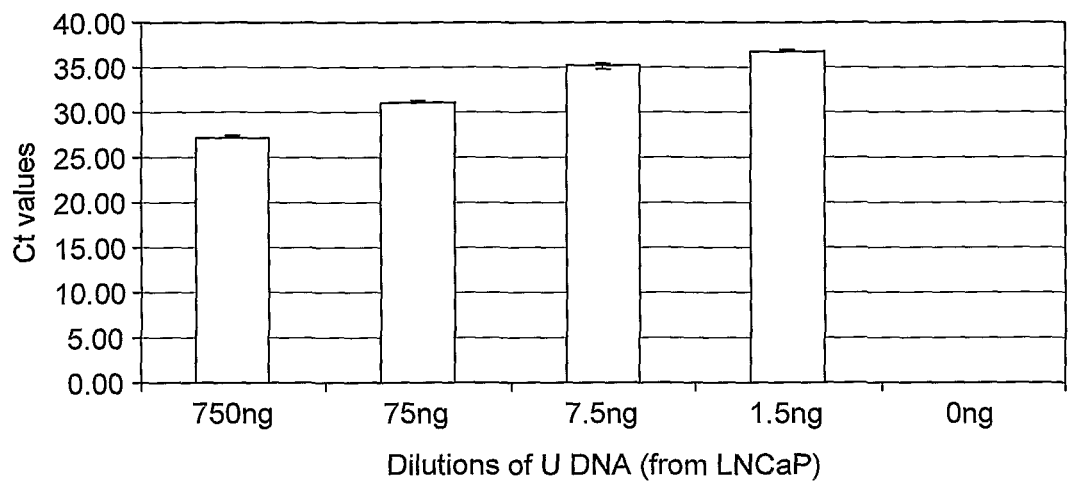
FIG. 3a: MAGEA3_GO_2_U: input U DNA (LNCaP cells) is plotted against Ct values, 1.5 ng of U input DNA is still detectable
Figure 3B:
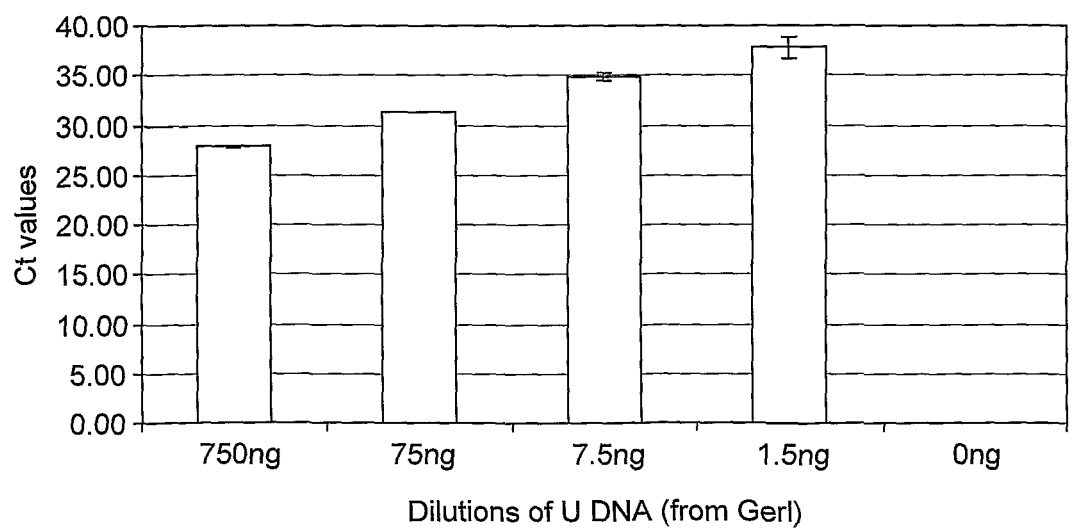
FIG. 3b: MAGEA3_Furuta_U: input U DNA (Gerl cells) is plotted against Ct values, 1.5 ng of U input DNA is still detectable

Subsequently 2.4 µl of the chemically treated DNA was used as template for MAGEA3 real-time MSP using specific primers for the unmethylated GO_2_U assay (LNCaP/DU145 DNA mixture) and unmethylated Furuta assay (Gerl/DU145 DNA mixture). Results are presented in FIG. 3.

As can be seen, the lower detection limit of the MAGEA3 GO_2_U and MAGEA3_Furuta real-time MSP was repeatedly set at 1.5 ng (1/500 dilution), this considering the whole sample preparation procedure. Since 10% of the sample is used per PCR reaction the final analytical sensitivity is 0.15 ng.

Analytical Specificity

The specificity of the MAGEA3 GO_1_U/GO_2_U/Furuta_U and QIU_U primer set was confirmed by MSP using CpGenome™ Universal Methylated/Unmethylated DNA (Chemicon International, Calif., USA; Cat. #S7821 and Cat. #S7822) and subsequent agarose gel analysis. Briefly, amplifluor real-time MSP was performed on the I Cycler (Bio-Rad) using the following thermal profile: Stage1: 50° C. for 2 min, Stage2: 95° C. for 10 min, Stage3: 95° C. for 15 sec, 62° C. for 1 min (=plateau-data collection) for 45 repeats. As a high specificity is essential for Amplifluor-based detection, a temperature gradient was applied in stage 3 to select for the best annealing temperature (57° C., 58.1° C., 60.3° C. and 61.8° C.).

All resulting PCR products were run on a 3% agarose gel. No band was visualized when CpGenome™ Universal Methylated DNA was used as template DNA (tested at 57° C.), confirming specificity for the Unmethylated DNA.

In addition, the specificity of the MAGEA3 assays was investigated amongst other gene members of the MAGE-A family using sequence alignment. The number of mismatches of the MAGE-A3 GO_1_U/GO_2_U/Furuta_U and QIU_U primerset vs. MAGE-A2 and MAGE-A12 sequences (converted sequences) is indicated in Table 3. The investigated U primers appeared specific for MAGE-A3 U/MAGE-A6 U.

TABLE 3

| Sequence alignment | | | |
|---|---|---|---|
| Assays: | Primers: | MAGE-A2 Mismatch | MAGE-A12 Mismatch |
| GO_1 U | Forward | 3 | 3 |
| | Reverse | 1 | 1 |
| | Total | 4 | 4 |
| GO_2 U | Forward | 6 | 6 |
| | Reverse | 0 | 0 |
| | Total | 6 | 6 |
| Furuta U | Forward | 1 | 2 |
| | Reverse | 1 | 1 |
| | Total | 2 | 3 |
| Qiu U | Forward | 6 | 6 |
| | Reverse | 6 | 6 |
| | Total | 12 | 12 |

Cloning MAGE-A3 Regulatory Sequences and Performance Standard Curve

A regulatory MAGE-A3 U DNA sequence of 364 bp was cloned using the flanking primers as indicated in Table 4.

TABLE 4

| Flanking primers used to generate MAGEA3 plasmid material | | | |
|---|---|---|---|
| Flanking primers | Target or gene name | Sense (S), Anti-sense (A) | Sequence 5' to 3' |
| MAGEA3_FL_1_S | MAGEA3 | S | ATTTTGAGGGATGATCGAAG (SEQ ID NO 23) |
| MAGEA3_FL_1_AS | MAGEA3 | A | CTAAAATAAAACCCGCCTCA (SEQ ID NO 24) |

This cloned material was used as standard curve material for Real Time MSP. The reproducibility was first confirmed by running 2 plates of 6 standard curves ($2*10^6$-$2*10^1$ copies) (2 different operators, 3 PCR mixes/operator/plate). Slope, PCR efficiency and $R^2$ values were monitored and gave acceptable results.

Performance Standard Curve.

A serial dilution of MAGEA3 plasmid material ($2\times10^6$ to $2\times10^1$ copies/5 µl) was loaded in duplicate using the specified primer and Amplifluor detector sequence in Table 1 with following optimized thermal profile: Stage1: 50° C. for 2 min, Stage2: 95° C. for 10 min, Stage3: 95° C. for 15 sec, 59° C. for 30 sec, 59° C. for 30 sec (=plateau-data collection) for 45 repeats. Results were generated using the SDS 2.2 software (Applied Biosystems), exported as Ct values (cycle number at which the amplification curves cross the threshold value, set automatically by the software). The performance of the standard curve is shown in Table 5

TABLE 5

| Summary of slopes and PCR efficiencies MAGEA3 | | | |
|---|---|---|---|
| Name | Slope | $R^2$ | Efficiency |
| MAGEA3_U set2 standard curve (plasmid) | 3.6736 | 0.9999 | 87.2% |
| MAGEA3_U set3 standard curve (plasmid) | 3.6994 | 0.9998 | 86.3% |
| MAGEA3_U set7 standard curve (plasmid) | 3.6108 | 0.9994 | 89.2% |
| MAGEA3_U set9 standard curve (plasmid) | 3.4885 | 0.9988 | 93.5% |
| MAGEA3_M set2 standard curve (plasmid) | 3.8601 | 0.9997 | 81.6% |
| MAGEA3_M set4 standard curve (plasmid) | 3.6701 | 0.9997 | 87.3% |

Example 4

Performance of the Assay on Cell Line Material

The MAGEA3 methylation status was investigated for 19 cell lines. The best methylated and unmethylated cell lines for the MAGEA3 U and M assay respectively are displayed below.

TABLE 6

Cell lines processed through MAGEA3 U assays

| Cell lines: | β-Actin | | Primers set U_2 | | | Primers set U_3 | | | Primers set U_7 | | |
| --- | --- | --- | --- | --- | --- | --- | --- | --- | --- | --- | --- |
| | Ct: | copies: | Ct: | copies: | ratios: | Ct: | copies: | ratios: | Ct: | copies: | |
| Gerl (108216) | 29.28 | 2086 | 29.57 | 1403 | 673 | 29.73 | 1753 | 841 | 26.97 | 2431 | 1166 |
| Staq (108217) | 28.09 | 4484 | 35.93 | 26 | 6 | UND | | | 34.41 | 16 | 4 |
| CRL9609 (108218) | 27.58 | 6192 | 32.47 | 225 | 36 | 34.98 | 73 | 12 | 29.80 | 358 | 58 |
| LNCaP | 28.82 | 2814 | 28.54 | 2684 | 954 | 28.64 | 3364 | 1195 | 25.88 | 5085 | 1807 |
| Du145 | 29.07 | 2393 | >40 | | | UND | | | >40 | | |
| HL60 | 28.29 | 3940 | 39.89 | 2.10 | 0.53 | >40 | | | >40 | | |

TABLE 7

Cell lines processed through MAGEA3 M assays

| Cell lines: | β-Actin | | Primers set M_2 | | | Primers set M_4 | | |
| --- | --- | --- | --- | --- | --- | --- | --- | --- |
| | Ct: | copies: | Ct: | copies: | ratios: | Ct: | copies: | ratios: |
| Gerl (108216) | 29.28 | 2086 | >40 | | | >40 | | |
| Staq (108217) | 28.09 | 4484 | 29.09 | 1388 | 309 | 27.54 | 2100 | 468 |
| CRL9609 (108218) | 27.58 | 6192 | 27.63 | 3363 | 543 | 26.89 | 3200 | 517 |
| LNCaP | 28.82 | 2814 | >40 | | | >40 | | |
| Du145 | 29.07 | 2393 | 29.72 | 945 | 395 | 28.96 | 839 | 351 |
| HL60 | 28.29 | 3940 | 28.97 | 1492 | 379 | 27.91 | 1657 | 421 |

Example 5

Intermediate Precision

The intermediate precision was tested by repeatedly performing the same assay for the unmethylated and methylated version of the MAGEA3 promoter sequence. Different numbers of fully modified MAGEA3 U and MAGEA3 M promoter DNA molecules (standard curve material) were measured repeatedly. In addition the operator factor was tested by having 2 different skilled laboratory people (operators A and B) perform the assay repeatedly on 2 different days (3 different standard curve dilutions in duplicate were run per operator per day).

Table 8 and 9 summarize experiments done to test the intermediate precision of the GO_1 and GO_2 U and M MAGEA3 assay. It was shown that the standard deviations of all results referring to the same numbers of molecules range between 0.11 and 1.29. A summary of all correlation coefficients (different operators and days) are shown in Table 9, average $R^2$ range between 0.9959 and 0.9997.

TABLE 8

Assays performed to test the intermediate precision (operator A and B on 2 different days): column 1: numbers of molecules (log), following colums: mean Ct values and standard deviation for each MAGEA3 assay

| Log copies | GO_1_U Average of all Ct values (SD) | GO_2_U Average of all Ct values (SD) | Furuta Average of all Ct values (SD) | GO_1_M Average of all Ct values (SD) | GO_2_M Average of all Ct values (SD) |
| --- | --- | --- | --- | --- | --- |
| 6.30 | 17.69 (0.27) | 19.31 (0.33) | 17.23 (0.84) | 17.78 (0.47) | 17.73 (0.12) |
| 5.30 | 21.41 (0.23) | 22.98 (0.37) | 20.70 (0.87) | 21.55 (0.44) | 21.32 (0.11) |
| 4.30 | 25.00 (0.27) | 26.64 (0.39) | 24.30 (0.86) | 25.36 (0.46) | 24.90 (0.11) |
| 3.30 | 28.70 (0.37) | 30.34 (0.68) | 27.85 (0.78) | 29.21 (0.36) | 28.51 (0.14) |
| 2.30 | 32.77 (1.28) | 34.06 (0.46) | 31.42 (0.85) | 33.26 (0.52) | 32.10 (0.38) |
| 1.30 | 36.24 (1.16) | 37.86 (1.29) | 34.97 (1.20) | 37.23 (1.20) | 35.75 (1.25) |
| | $R^2 = 0.9997$ | $R^2 = 1.000$ | $R^2 = 1.000$ | $R^2 = 0.9998$ | $R^2 = 1.000$ |

TABLE 9

Correlation coefficients found for each analyzed dilution series.

| day | operator | points | R² GO_1_U | R² GO_2_U | R² Furuta | R² GO_1_M | R² GO_2_M |
|---|---|---|---|---|---|---|---|
| 1 | A | 6 | 0.9993 | 0.9974 | 0.9999 | 0.9972 | 0.9996 |
| 1 | A | 6 | 0.9993 | 0.9998 | 0.9993 | 0.9991 | 0.9992 |
| 1 | A | 6 | 0.9997 | 0.9969 | 0.9992 | 0.9988 | 0.9994 |
| 1 | B | 6 | 0.9997 | 0.9989 | 0.9999 | 0.9996 | 0.9999 |
| 1 | B | 6 | 0.9996 | 0.9971 | 0.9998 | 0.9986 | 0.9996 |
| 1 | B | 6 | 0.9983 | 0.9987 | 0.9999 | 0.9998 | 0.9959 |
| 2 | A | 6 | 0.9950 | 0.9996 | 0.9997 | 0.9989 | 0.9912 |
| 2 | A | 6 | 0.9988 | 0.9966 | 0.9998 | 0.9990 | 0.9994 |
| 2 | A | 6 | 0.9997 | 0.9957 | 0.9996 | 0.9970 | 0.9997 |
| 2 | B | 6 | 0.9995 | 0.9994 | 0.9999 | 0.9976 | 0.9980 |
| 2 | B | 6 | 0.9975 | 0.9997 | 0.9998 | 0.9998 | 0.9999 |
| 2 | B | 6 | 0.9648 | 1.0000 | 0.9992 | 0.9976 | 0.9999 |
| | | | Average 0.9959 | Average 0.9983 | Average 0.9997 | Average 0.9986 | Average 0.9985 |

Example 6

Melanin Interference

Previously it has been reported that the efficiency of PCRs from samples containing melanin was low.

Eckhart et al. (2000) found that both RNA and cDNA preparations derived from melanocytes contain a RT-PCR inhibitor that copurified with nucleic acids. Investigation of the candidate inhibitor melanin revealed that it reversibly binds to thermostable DNA polymerase and inhibits its activity. Before processing melanoma samples through the MAGEA3 U amplifluor assays, the potential inhibition by melanin was investigated.

Synthetic melanin was prepared as described by Eckhart et al. Briefly, melanin (SIGMA M8631) was dissolved in distilled water at a concentration of 2 mg/ml, vortexed extensively and sonicated in a water bath at room temperature for 10 min. The non-dissolved melanin was removed by centrifugation at 9000 g. The potential inhibition effect was tested by adding melanin at different steps of the reaction process:

1) Before extraction: 1 µg and 5 µg of prepared melanin was added to 250,000 LNCaP cells and 250,000 MCF7 cells
2) After extraction: 1 µg and 5 µg of prepared melanin was added to 1 µg of LNCap and MCF7 DNA
3) After bisuphite treatment: 1 µg and 5 µg of prepared melanin was directly spiked in the PCR reaction. Bisulphite elution volumes were adapted to have either a constant template concentration (annotated as 'a', e.g. LNCaP a) or a constant amount of template in the PCR reaction (annotated as 'b', e.g. LNCaP b).

These melanin containing LNCaP and MCF7 samples were simultaneously processed with corresponding non-spiked melanin samples.

Samples were processed further using PUREGENE® DNA Purification Kit and EZ DNA Methylation kit. The chemically modified DNA was used as input material for MAGEA3 U, Gst-Pi M and ACTB real-time MSP.

Recovered copy numbers of the tested gene promoter and ACTB reference gene were calculated and compared for each condition.

Figure 9A:
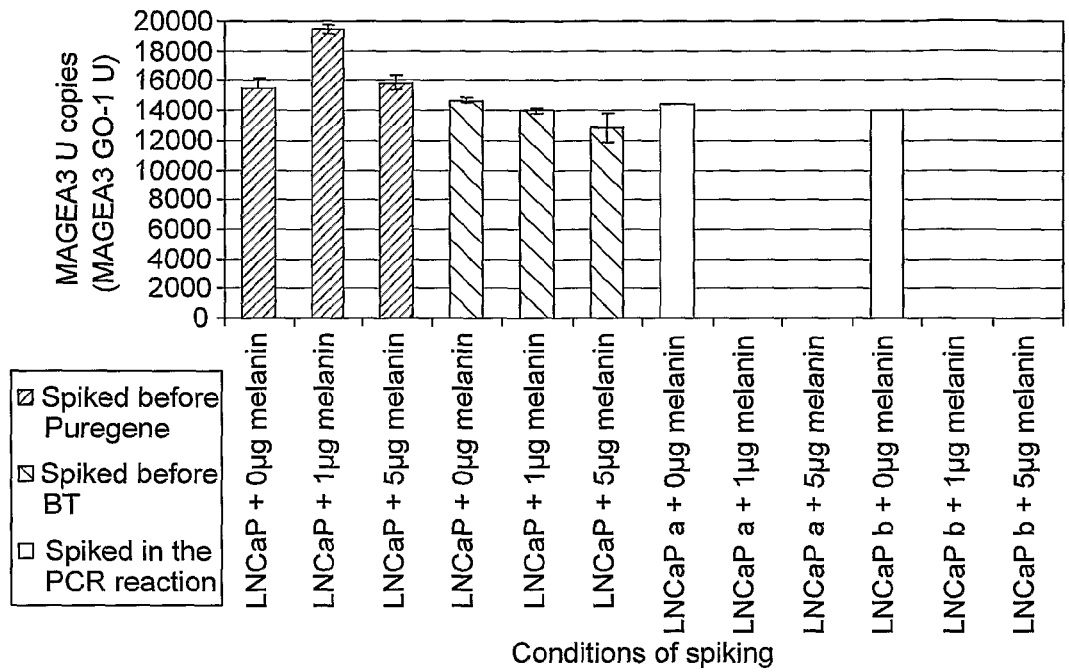
FIG. 9a: LNCaP cell line material with and without spiked melanin processed through MAGE-A3 U real-time MSP. BT=bisulphite treatment.
Figure 9B:
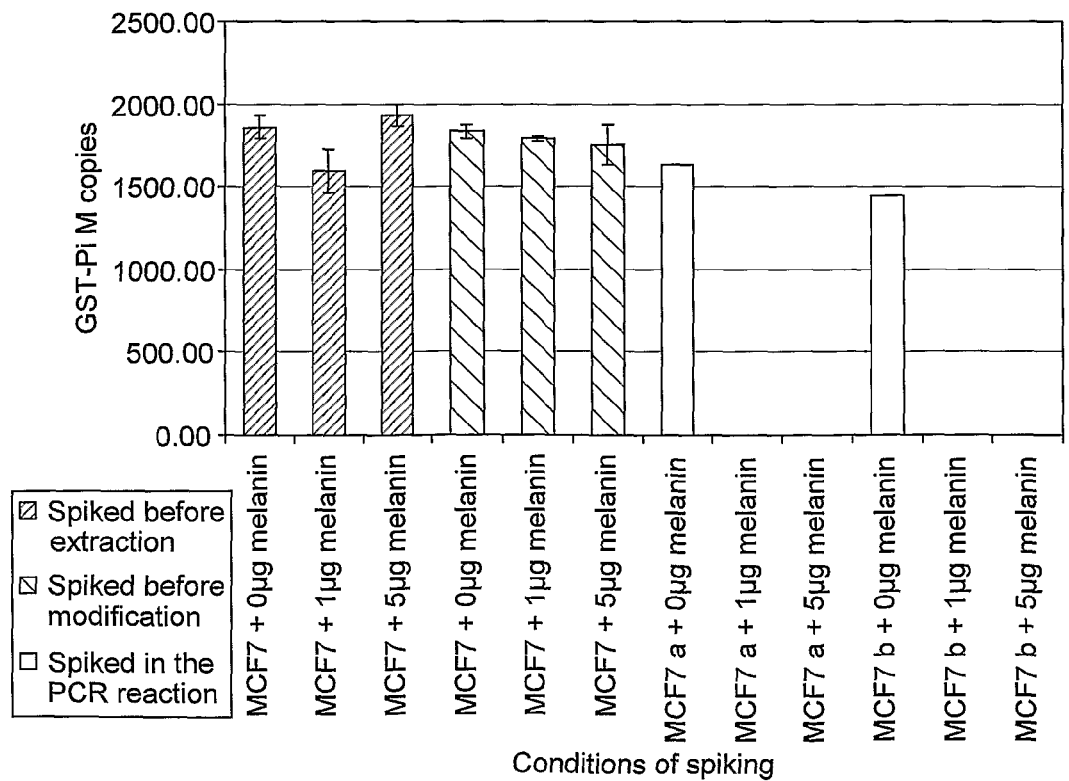
FIG. 9b: MCF7 cell line material with and without spiked melanin processed through Gst-Pi M real-time MSP

Results are shown in FIG. 9. No significant PCR inhibitory effect was observed when melanin was added before or after DNA extraction. Melanin only showed clear inhibition when directly spiked into the PCR reaction. Contrary to RT-PCR, melanoma samples with high melanin content can be processed through real-time MSP without risk of PCR inhibition.

Example 7

MAGE-A3 Methylation Status in Melanoma/Lung Samples and Concordance with RNA Expression Materials and Methods Clinical Samples Surgical specimens from melanoma and lung cancer patients were provided by GSKBio: genomic DNA samples (gDNA), biopsy material in RNA Later® solution and corresponding formalin fixed paraffin embedded tissue (FFPE) were classified as MAGEA3 positive or MAGEA3 negative based on GSKBio RNA expression data. An overview of the provided sample set is detailed in Table 10.

TABLE 10

Clinical sample collection

| Diagnosis group | Sample type | Number of samples | MAGEA3 RNA expression classification by RT-PCR |
|---|---|---|---|
| Melanomas | gDNA | 41 | 24 positive |
| | | | 17 negative |
| NSCLC | tissue in RNA later ® | 61 | 26 positive |
| | | | 35 negative |
| NSCLC | FFPE | 52 | 26 positive* |
| | | | 26 negative* |

*classification was made based on the corresponding RNA later ® tissue

Cell Lines:

Cell lines were included in each run as positive and negative controls. Before applying the amplifluor real-time MSP assay on clinical samples, the sensitivity and specificity of the assay was affirmed on cell line material. The best MAGEA3 methylated and unmethylated cell lines are summarized in Table 11. Gerl, Staq en CRL9609 were obtained from GSK-Bio, cell lines LNCaP and DU145 were purchased from the American Type Culture Collection.

TABLE 11

MAGEA3 control cell lines

|  | MAGEA3 RNA expression status | MAGEA3 methylation status |
|---|---|---|
| Gerl | Positive | unmethylated |
| Staq | Negative | methylated |
| CRL9609 | Negative | methylated |
| LNCaP | Not tested | unmethylated |
| DU145 | Not tested | methylated |

DNA Isolation:

Formalin Fixed paraffin embedded samples were first de-paraffinized in 750 µl xylene for 2 h. A second xylene treatment was done (400 µl xylene for 2 h) Then, 250 µl of 70% ethanol was added before centrifugation at 13000 rpm for 15 min. The supernatant was removed and the samples were air dried at room temperature.

The samples in RNA Later® were cut in very small pieces using a razor blade after removal of the RNA Later® solution.

Subsequently, the DNA was extracted using the classical phenol/chloroform extraction method and resuspended in 50 µl LoTE (3 mM TRIS, 0.2 mM EDTA, pH 8.0).

DNA was quantified using the Picogreen® dsDNA quantitation kit (Molecular Probes, #P7589) following the manufacturer's recommendations. λDNA provided with the kit was used to prepare a standard curve. The data were collected using a FluoStar Galaxy plate reader (BMG Lab technologies, Germany).

DNA modification: 1.5 µg of DNA was subjected to bisulphite modification using the EZ DNA Methylation kit from Zymo Research.

Briefly, aliquots of 45 µl were mixed with 5 µl of M-Dilution Buffer and incubated at 37° C. for 15 min shaking at 1100 rpm. Then 100 µl of the diluted CT Conversion Reagent was added and samples were incubated at 70° C. for 3 h, shaking at 1100 rpm in the dark. After conversion, the samples were further desalted and desulfonated according to manufacturer's instructions and eluted in 25 µl Tris-HCl 1 mM pH8.0. The modified DNA was stored at −80° C. until further processing.

DNA amplification: Real-time MSP was applied on a 7900HT fast real-time PCR cycler from Applied Biosystems.

Four MAGEA3 hypomethylation assays, designed to target the unmethylated version of the gene promoter sequence were tested for concordance with the provided RNA expression data, which was measured in accordance with methods described in WO2007/147876, for example, using the primers and probe of Table 2, Exon 3 MAGE-A3 specific primers and probe of SEQ ID NO:3, 4 and 13. The independent reference gene β-actin (ACTB) was also measured. Primer and amplifluor detector sequences are shown in Table 1.

2.4 µl of the modified genomic DNA sample was added to a final 12 µl PCR reaction volume including: 6 µl of iTaq™ Supermix with Rox (BioRad, 2× buffer) and final primer concentrations of 100 nM for both forward primer/detector and reverse primer. Cycling conditions for each MAGEA3 design were 50° C. for 2 min; 95° C. for 10 min; followed by 45 cycles of 95° C. for 15 sec, 59° C. for 30 sec [62° C. for ACTB] and 59° C. for 30 sec [62° C. for ACTB] (=plateau-data collection).

Results were generated using the SDS 2.2.2 software (Applied Biosystems), exported as Ct values (cycle number at which the amplification curves cross the threshold value, set automatically by the software), and then used to calculate copy numbers based on a linear regression of the values plotted on a standard curve of 20–2×10^6 gene copy equivalents, using plasmid DNA or purified PCR products containing the bisulphite modified sequence of interest. The ratio between MAGEA3 and ACTB was calculated to generate the test result. In order to interpret the data, a clinical cutoff (threshold) was defined based on the un-blinded RNA expression data.

Figure 5:
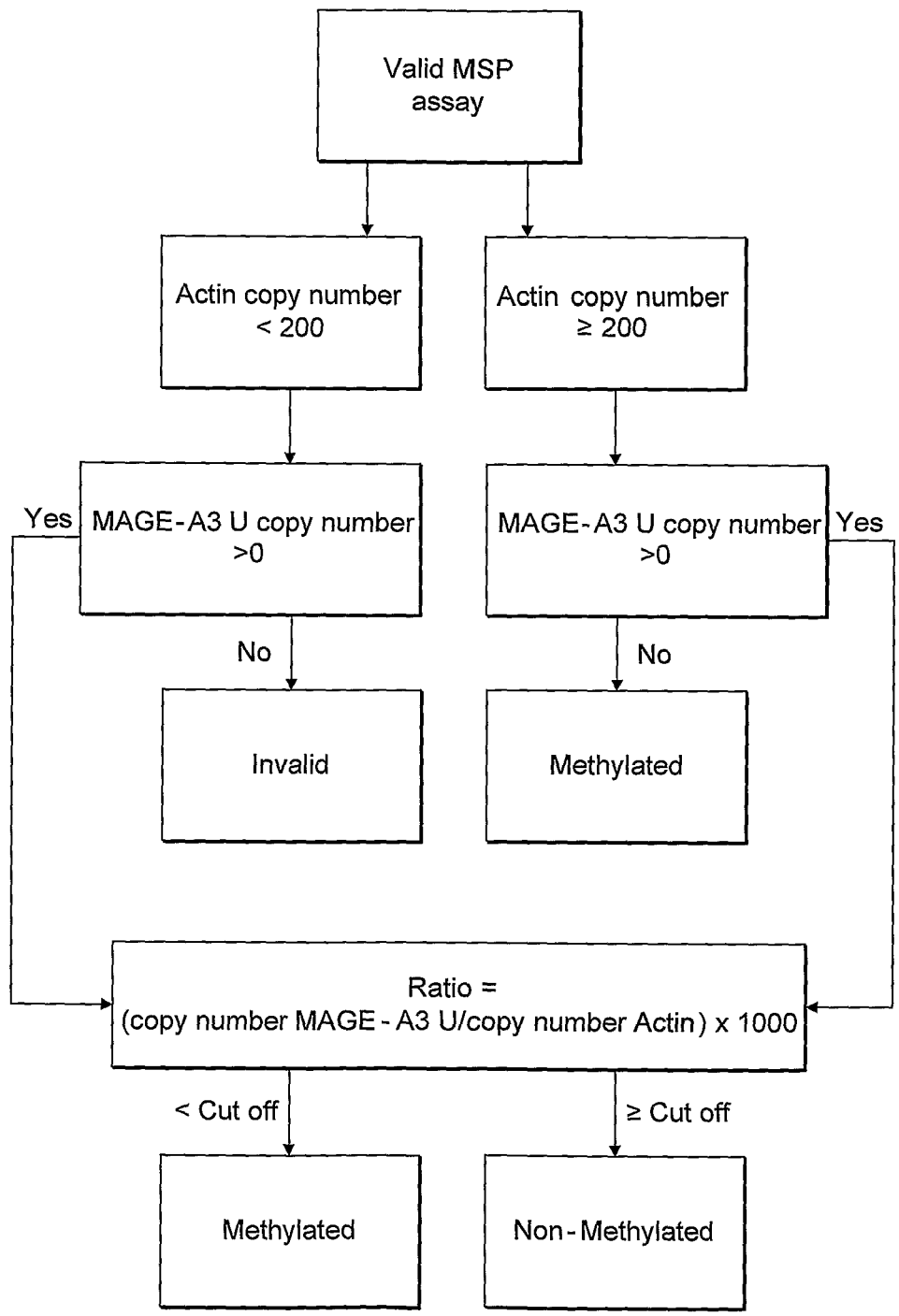
FIG. 5: Decision tree for sample classification (Methylated, Non-Methylated or Invalid)
Figure 6A:
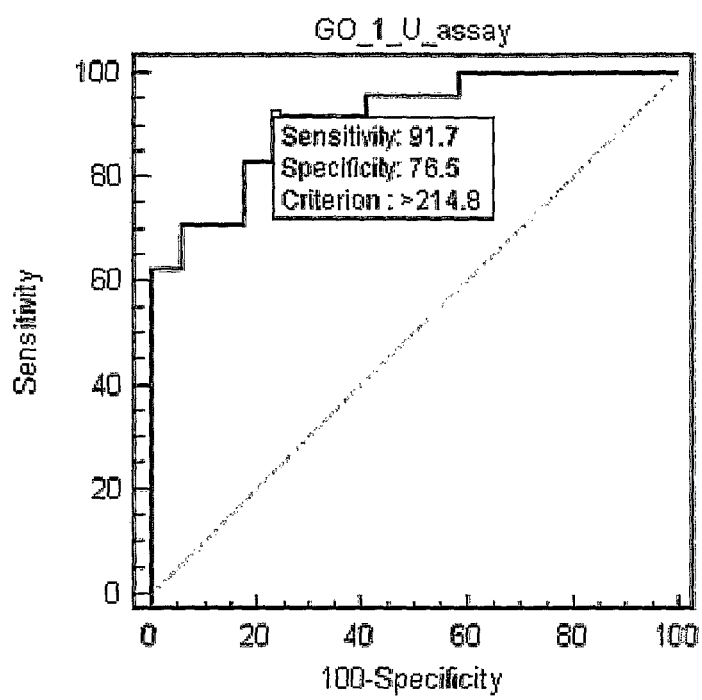
FIG. 6a: GO_1_U assay: sensitivity 91.7%, specificity 76.5%, cut-off 214.8, Area under the curve (AUC) is 0.912. The 95% CI range was 0.781 to 0.977 at a significance of P=0.0001 for area=5.
Figure 6B:
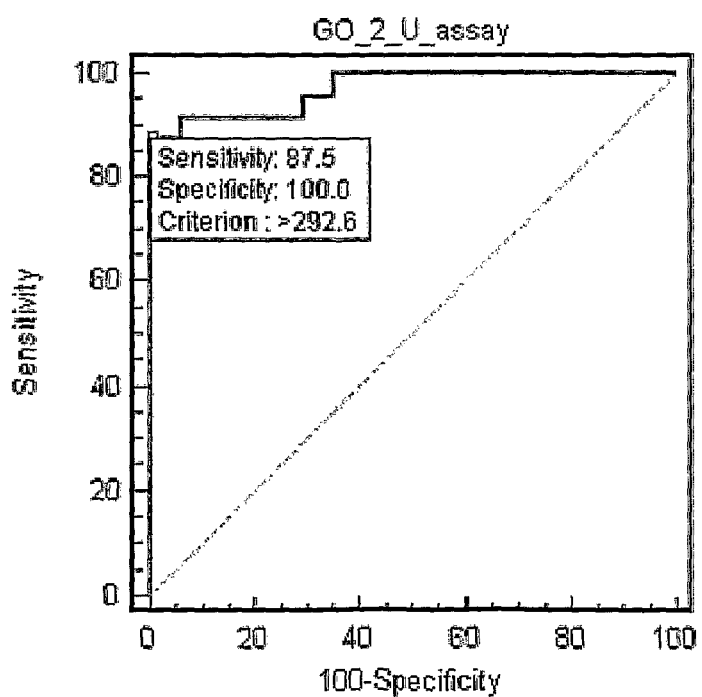
FIG. 6b: GO_2_U assay: sensitivity 87.5%, specificity 100%, cut-off 292.6, Area under the curve (AUC) is 0.971. The 95% CI range was 0.863 to 0.996 at a significance of P=0.0001 for area=5.
Figure 6C:
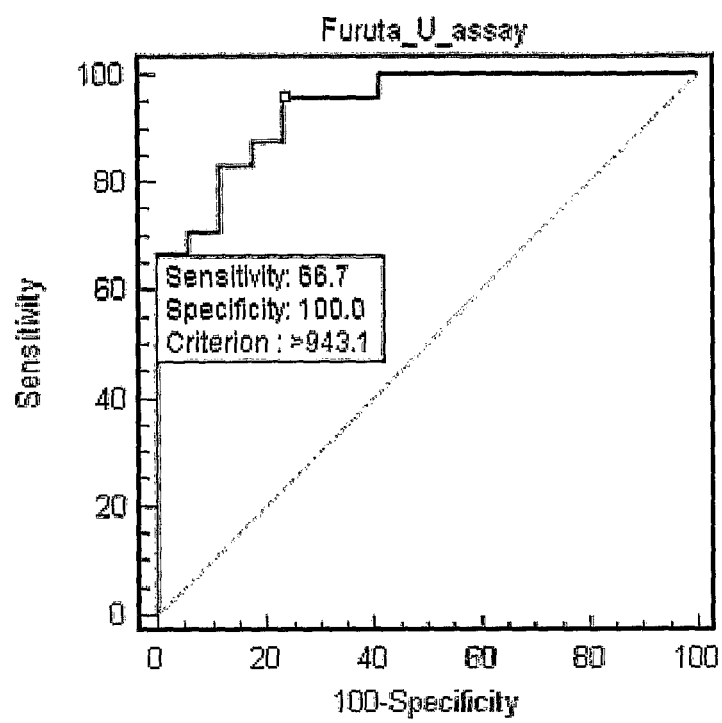
FIG. 6c: Furuta_U assay: sensitivity 66.7%, specificity 100%, cut-off 943.1, Area under the curve (AUC) is 0.939. The 95% CI range was 0.817 to 0.989 at a significance of P=0.0001 for area=5.
Figure 6D:
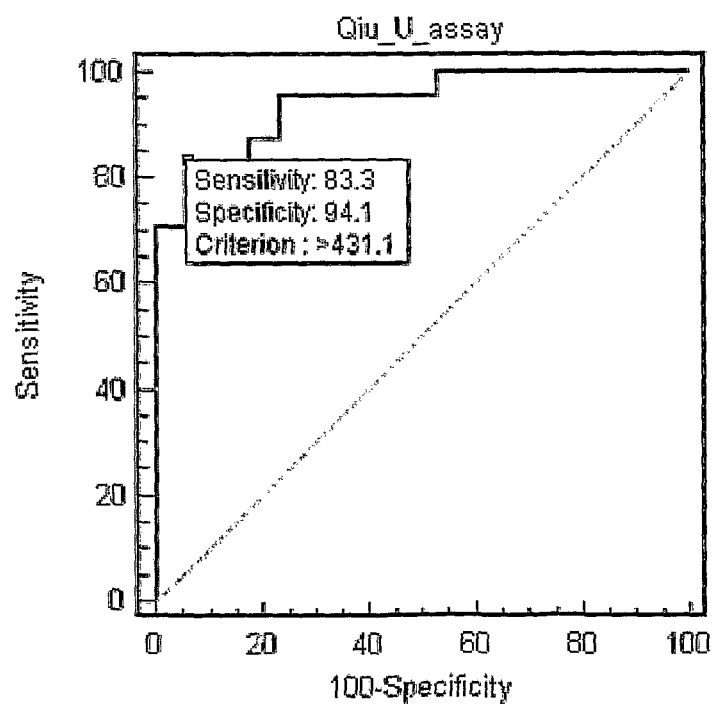
FIG. 6d: Qiu_U assay: sensitivity 83.3%, specificity 94.1%, cut-off 431.1, Area under the curve (AUC) is 0.944. The 95% CI range was 0.824 to 0.990 at a significance of P=0.0001 for area=5.
Figure 7A:
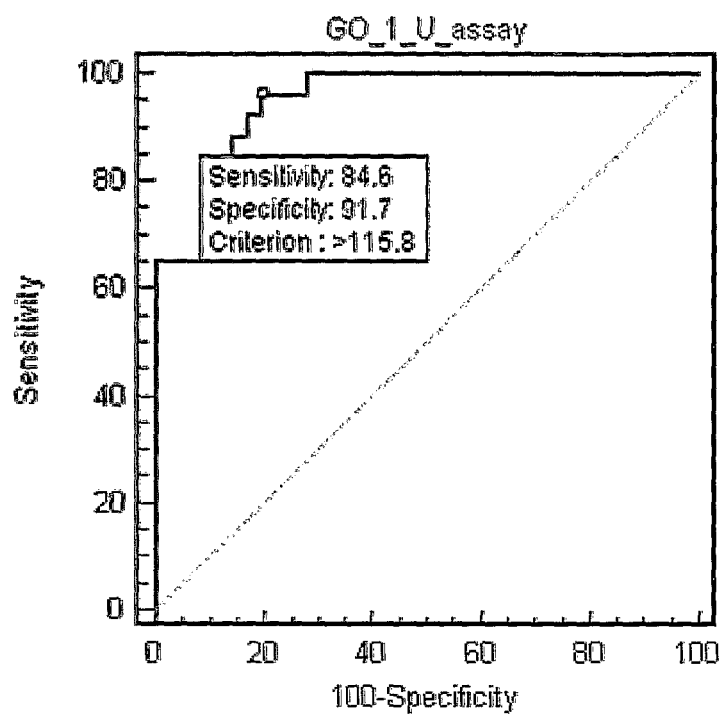
FIG. 7a: GO_1_U assay: sensitivity 84.6%, specificity 91.7%, cut-off 115.8, Area under the curve (AUC) is 0.954. The 95% CI range was 0.868 to 0.990 at a significance of P=0.0001 for area=5.
Figure 7B:
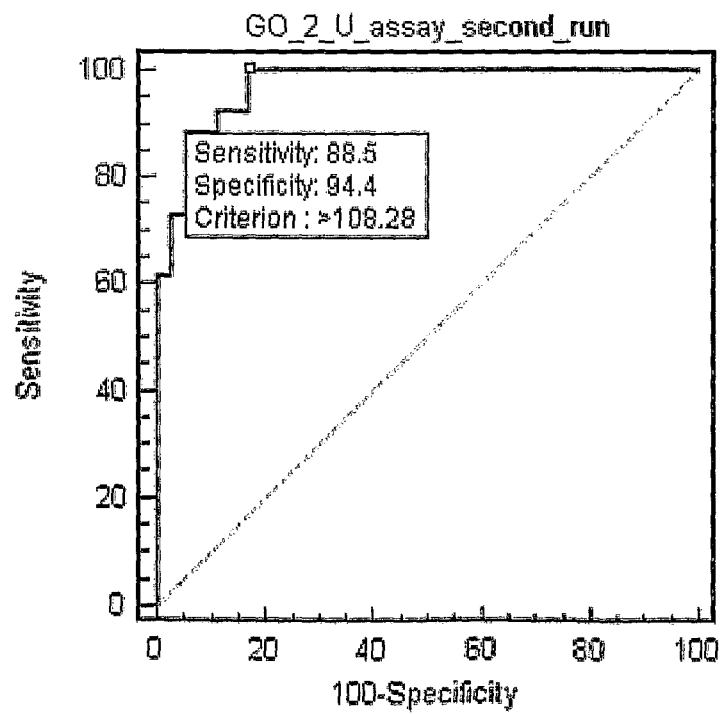
FIG. 7b: GO_2_U assay: sensitivity 88.5%, specificity 94.4%, cut-off 108.28, Area under the curve (AUC) is 0.971. The 95% CI range was 0.893 to 0.996 at a significance of P=0.0001 for area=5.
Figure 7C:
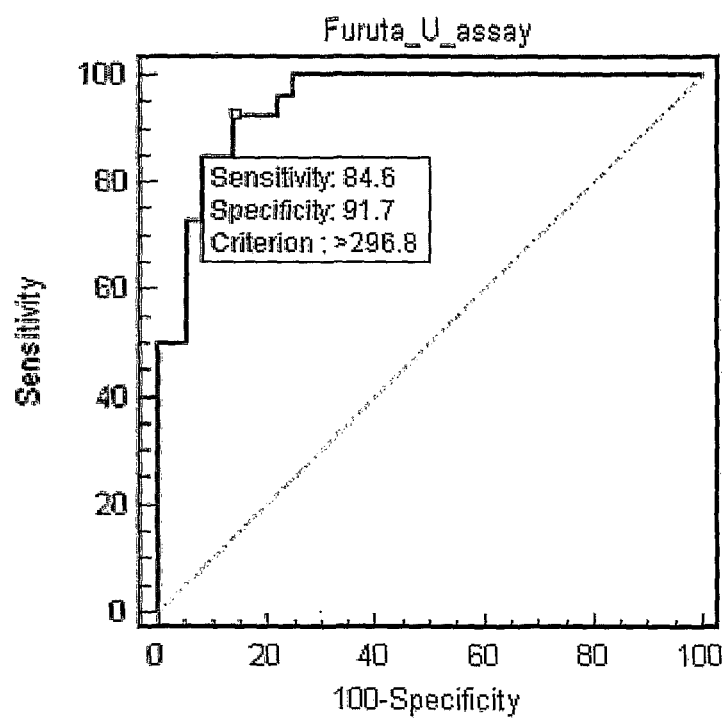
FIG. 7c: Furuta_U assay: sensitivity 84.6%, specificity 91.7%, cut-off 296.8, Area under the curve (AUC) is 0.949. The 95% CI range was 0.861 to 0.988 at a significance of P=0.0001 for area=5.
Figure 7D:
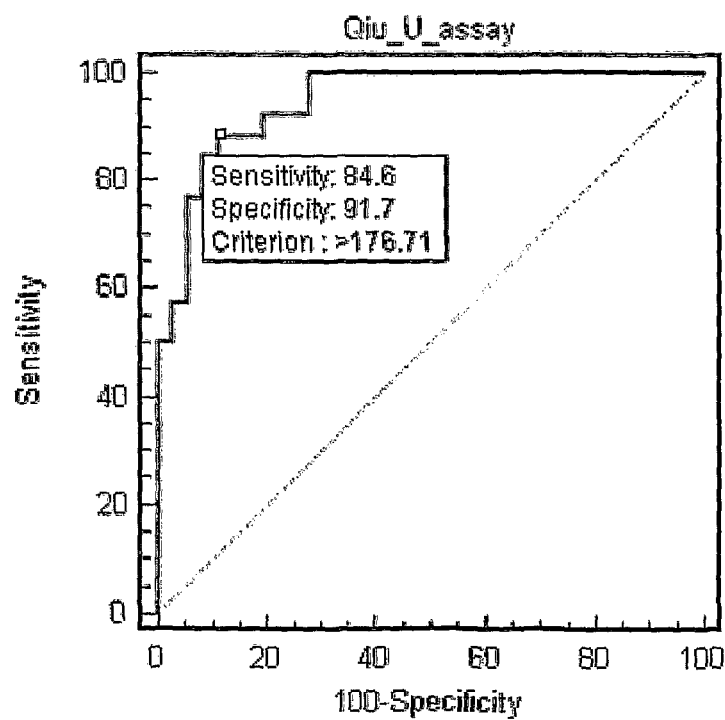
FIG. 7d: Qiu_U assay: sensitivity 84.6%, specificity 91.7%, cut-off 176.71, Area under the curve (AUC) is 0.948. The 95% CI range was 0.859 to 0.988 at a significance of P=0.0001 for area=5.
Figure 8A:
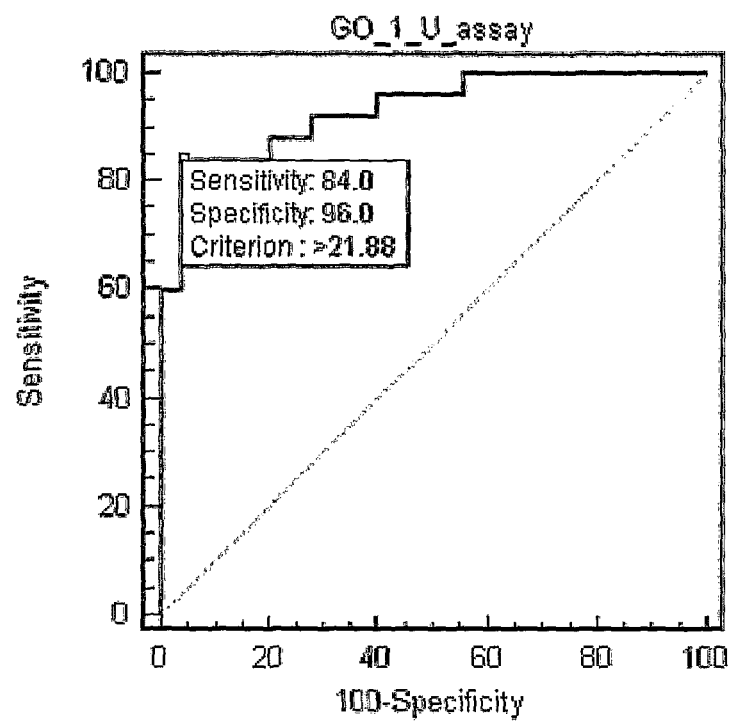
FIG. 8a: GO_1_U assay: sensitivity 84.0%, specificity 96.0%, cut-off 21.88, Area under the curve (AUC) is 0.933. The 95% CI range was 0.825 to 0.984 at a significance of P=0.0001 for area=5.
Figure 8B:
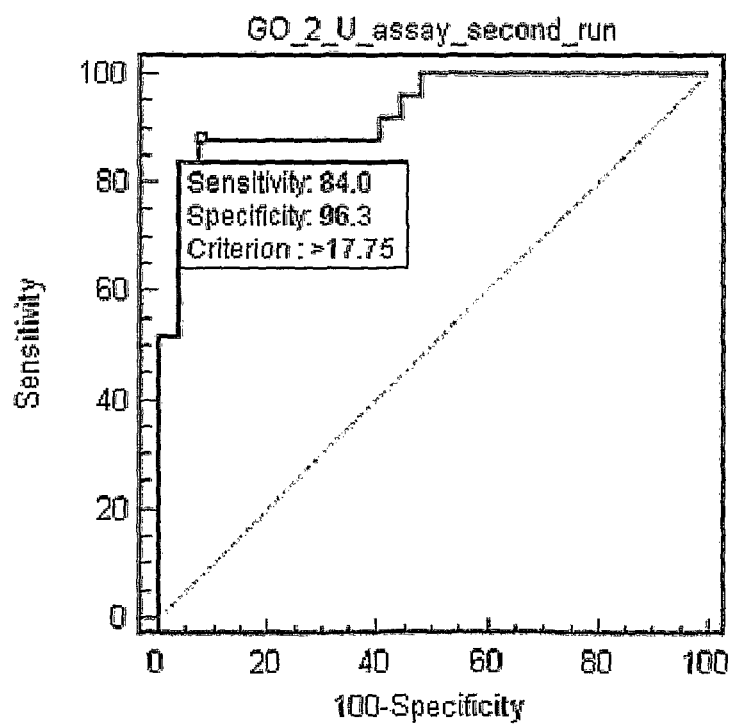
FIG. 8b: GO_2_U assay: sensitivity 84.0%, specificity 96.3%, cut-off 17.75, Area under the curve (AUC) is 0.932. The 95% CI range was 0.826 to 0.983 at a significance of P=0.0001 for area=5.
Figure 8C:
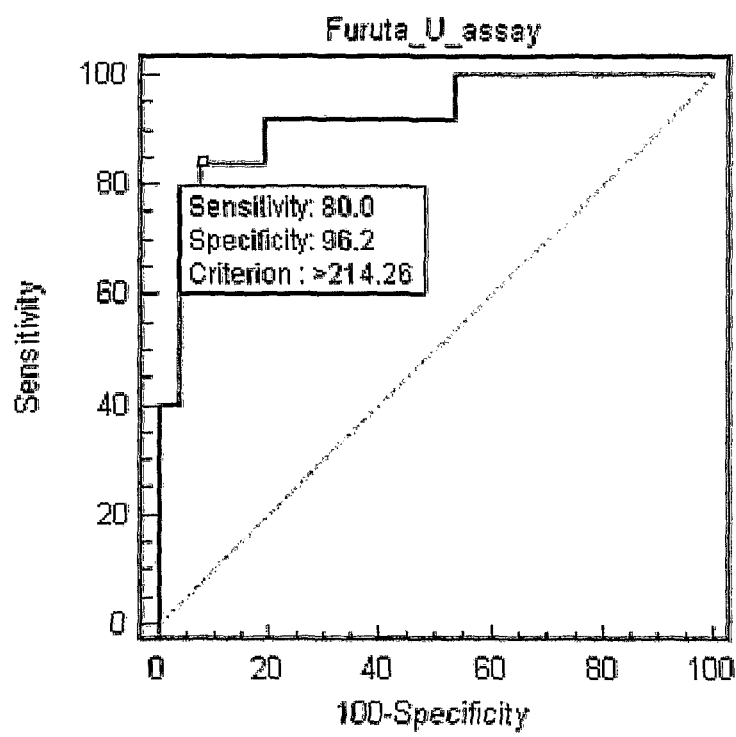
FIG. 8c: Furuta_U assay: sensitivity 80.0%, specificity 96.2%, cut-off 214.26, Area under the curve (AUC) is 0.923. The 95% CI range was 0.813 to 0.979 at a significance of P=0.0001 for area=5.
Figure 8D:
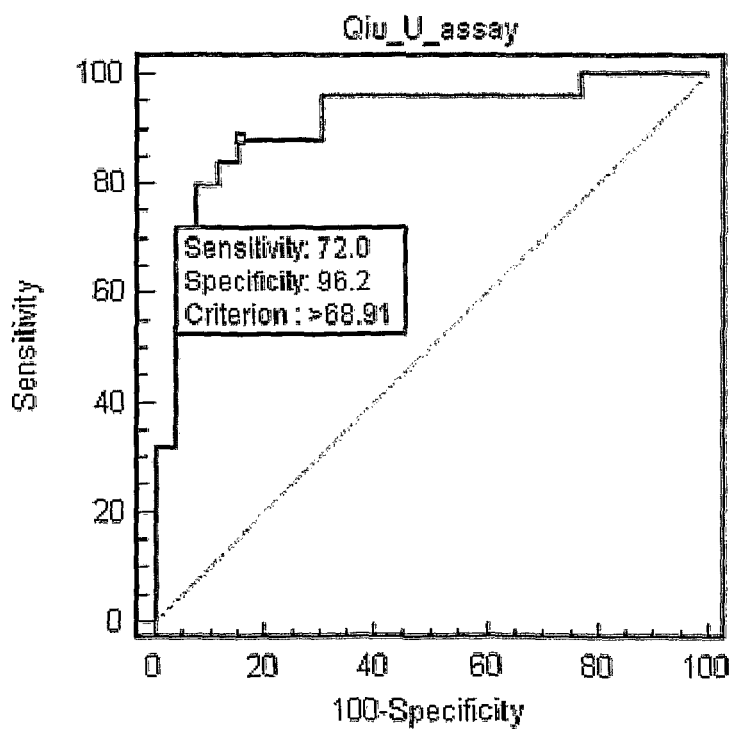
FIG. 8d: Qiu_U assay: sensitivity 72.0%, specificity 96.2%, cut-off 68.91, Area under the curve (AUC) is 0.912. The 95% CI range was 0.799 to 0.973 at a significance of P=0.0001 for area=5.

The samples were classified as methylated, non-methylated, or invalid based on the decision tree shown in FIG. 5. Cell lines were included in each run as positive and negative controls, and entered the procedure at the DNA extraction step.

A run was considered valid when the following criteria were met: a) PCR efficiency of both standard curves above 80%; b) r^2 of at least 4 relevant data points above 0.990; c) Δ Ct between duplicates <1.5; d) routinely included NTC not amplified; e) 10% of a 1.5 µg conversion reaction of the positive cell line assay control was detectable; and f) 10% of a 1.5 µg conversion reaction of the negative cell line assay control was not detected within the standard curve.

Results

Concordance Between Methylation and Gene Expression:

Melanomas:

Expression and methylation levels of MAGEA3 were compared on a same sample set. In total, 41 melanoma samples were processed using RT-PCR and real-time MSP. Several designs of the MAGEA3 U amplifluor assay were tested to see which assay accorded best with the RNA expression data provided by GSK. The clinical cut-off was set in such a way having maximum concordance and minimum of false positives (see Table 12). ROC curves for the MAGEA3 methylation status in these samples are shown in FIG. 6. Among the 17 negative samples, 9 were positive for other MAGE-A family members; the GO_2_U and Furuta U assay correctly classified these 9 samples (specificity of 100%).

Taken all this data together, the MAGEA3_GO_2_U assay performed best with a 92.7% concordance and 100% specificity.

TABLE 12

Concordance data melanoma samples

|  | MAGEA3_GO_1_U | MAGEA3_GO_2_U | MAGEA3 Furuta U | MAGEA3 Qiu U |
|---|---|---|---|---|
| Cut off | 315 | 330 | 946 | 434 |
| Correctly classified, for MAGEA3 negatives (GSK → 17) | 13 | 17 | 17 | 16 |
| Correctly classified for MAGEA3 positives (GSK → 24) | 22 | 21 | 16 | 20 |

TABLE 12-continued

Concordance data melanoma samples

|  | MAGEA3_GO_1_U | MAGEA3_GO_2_U | MAGEA3 Furuta U | MAGEA3 Qiu U |
|---|---|---|---|---|
| Correctly classified samples (total samples: 41) | 35 | 38 | 33 | 36 |
| Concordance | 85.4% | 92.7% | 80.5% | 87.8% |

Lung Samples (Biopsies and FFPE):

The same set up as above was tested on a different sample set: 52 lung FFPE samples and 61 lung tissues in RNA Later® were screened through the 4 MAGEA3 U amplifluor assays and accorded with corresponding RNA data.

ROC curves for the MAGEA3 methylation status in these lung biopsy and FFPE samples are presented in FIGS. 7 and 8 respectively. Among the MAGEA3 negative samples, 9 were positive for other MAGE-A family members; the MAGEA3 U assays correctly classified all 9 samples (specificity of 100%). Obtained results confirmed that the MAGEA3_G_2_U assay was the best performing assay with a concordance of 90.4% in FFPE and a concordance of 91.8% in biopsies, maintaining a specificity of 100% (Table 13).

TABLE 13

Concordance data lung samples (MAGEA3_GO_2_U assay)

|  | MAGEA3_GO_2_U | |
|---|---|---|
|  | FFPE | Biopsies |
| Cut off | 29 | 112 |
| Correctly classified for MAGEA3 negatives (GSK) | 26/26 | 33/35 |
| Correctly classified for MAGEA3 positives (GSK) | 21/26 | 23/26 |
| Correctly classified | 47 | 56 |
| Total samples | 52 | 61 |
| Concordance | 90.4% | 91.8% |

Example 8

Testing of Lung Samples Through MAGEA3 Assays

DNA from lung cancers was processed through MAGEA3 (U & M assay versions) and β-actin assays in parallel with LNCaP & DU145 control cell lines. Several designs of MAGEA3 U amplifluor assay were tested to see which assay accorded best with the MAGEA3 GO_2 U assay. Experimental conditions as described in example 7 were used. Standard curves showed efficiencies above 80%. $R^2$ was higher than 0.99. Cut off values were set at 29 for the MAGEA3 GO_2 U assay; 22 for the MAGEA3 GO_1 U assay; 229 for the MAGEA3 Furuta U assay; 87 for the MAGEA3 Qiu assay; 148 or the MAGEA3 GO_1 M assay and 167 for the MAGEA3 GO_2 M assay. Methylation levels of MAGEA3 were compared on the same sample set.

Results are shown in Tables 14 and 15. For the MAGEA3 GO_2 U assay (cut off=29):
- 3 samples are classified as invalid and those samples are not included for the comparison with the others U & M assays;
- 9 samples are classified as non-methylated;
- 15 samples are classified as methylated.

The four MAGEA3 U assays give similar results with 96% of concordance with the MAGEA3 GO_2 U assay for the valid samples. The MAGEA3 M assays gave 71% and 75% concordance with the MAGEA3 GO_2 U assay.

TABLE 14

Summary table comparing the different U assays and showing the concordances calculated for the U assays compared to GO_2 U assay (this table takes only the valid samples into account).

|  | MAGEA3 U set 3 (GO 2 U) | MAGEA3 U set 2 (GO 1 U) | MAGEA3 U set 7 (Furuta U, REPEAT) | MAGEA3 U set 9 (Qiu U) |
|---|---|---|---|---|
| METHYLATED (/15): | 15 | 14 | 14 | 14 |
| NON-METHYLATED (/9): | 9 | 9 | 9 | 9 |
| TOTAL | 24 | 23 | 23 | 23 |
| Concordance: | 100% | 96% | 96% | 96% |

TABLE 15

Summary table comparing the different M assays and showing the concordances calculated for the M assays

|  | MAGEA3 U set 3 (GO 2 U) | MAGEA3 M set 2 (GO 1 M) | MAGEA3 M set 4 (GO 2 M) |
|---|---|---|---|
| METHYLATED (/15): | 15 | 11 | 13 |
| NON-METHYLATED (/9): | 9 | 6 | 5 |
| TOTAL | 24 | 17 | 18 |
| Concordance: | 100% | 71% | 75% | compared to GO_2 U assay (this table takes only the valid samples into account).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A primer pair comprising oligonucleotides or primers consisting of the nucleotide sequence of SEQ ID NO. 6 and 7.

2. A kit for detecting the methylation status of the MAGE-A3 gene comprising the primer pair of claim 1.

3. A method of detecting unmethylated Mage-A3 gene in a DNA-containing sample, comprising:
   (a) contacting and treating the DNA-containing sample with a reagent which selectively modifies unmethylated cytosine residues in the DNA to produce detectable modified residues but which does not modify methylated cytosine residues
   (b) amplifying at least a portion of the unmethylated gene of interest using the primer pair of claim 1.

4. A primer pair comprising oligonucleotides or primers consisting of the nucleotide sequence of SEQ ID NO 2 and 3.

5. A kit for detecting the methylation status of the MAGE-A3 gene comprising the primer pair of claim 4.

6. A method of detecting umethylated Mage-A3 gene in a DNA-containing sample, comprising:
   (a) contacting and treating the DNA-containing sample with a reagent which selectively modifies unmethylated cytosine residues in the DNA to produce detectable modified residues but which does not modify methylated cytosine residues
   (b) amplifying at least a portion of the unmethylated gene of interest using the primer pair of claim 4.

* * * * *

SEQUENCE LISTING

<160> NUMBER OF SEQ ID NOS: 41

<210> SEQ ID NO 1
<211> LENGTH: 22
<212> TYPE: DNA
<213> ORGANISM: Artificial sequence
<220> FEATURE:
<223> OTHER INFORMATION: Oligonucleotide (hairpin)

<400> SEQUENCE: 1
agcgatgcgt tcgagcatcg cu                                             22

<210> SEQ ID NO 2
<211> LENGTH: 24
<212> TYPE: DNA
<213> ORGANISM: Artificial sequence
<220> FEATURE:
<223> OTHER INFORMATION: Primer

<400> SEQUENCE: 2
atttttgttt ggaatttagg gtag                                           24

<210> SEQ ID NO 3
<211> LENGTH: 43
<212> TYPE: DNA
<213> ORGANISM: Artificial sequence
<220> FEATURE:
<223> OTHER INFORMATION: Hairpin primer

<400> SEQUENCE: 3
agcgatgcgt tcgagcatcg cuccaacatc aaaccatcac tca                      43

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
ccaacatcaa accatcactc a                                              21

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
tggaatttag ggtagtattg t                                              21

<210> SEQ ID NO 6
<211> LENGTH: 43
<212> TYPE: DNA
<213> ORGANISM: Artificial sequence
<220> FEATURE:
<223> OTHER INFORMATION: Hairpin primer

<400> SEQUENCE: 6
agcgatgcgt tcgagcatcg cutggaattt agggtagtat tgt                      43

<210> SEQ ID NO 7
<211> LENGTH: 18
<212> TYPE: DNA

```
<213> ORGANISM: Artificial sequence
<220> FEATURE:
<223> OTHER INFORMATION: Primer

<400> SEQUENCE: 7
ccctccacca acatcaaa                                                   18

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
ttaggatgtg atgttattga tttgt                                           25

<210> SEQ ID NO 9
<211> LENGTH: 47
<212> TYPE: DNA
<213> ORGANISM: Artificial sequence
<220> FEATURE:
<223> OTHER INFORMATION: Primer

<400> SEQUENCE: 9
agcgatgcgt tcgagcatcg cuttaggatg tgatgttatt gatttgt                   47

<210> SEQ ID NO 10
<211> LENGTH: 203
<212> TYPE: DNA
<213> ORGANISM: Artificial sequence
<220> FEATURE:
<223> OTHER INFORMATION: Portion of MAGE-A3 unconverted sequence

<400> SEQUENCE: 10
catgcttacc tccacccca tccgatcccc atccaggcag aatccagttc caccctgcc       60 cggaacccag ggtagtaccg ttgccaggat gtgacgccac tgacttgcgc attggaggtc    120
agaagaccgc gagattctcg ccctgagcaa cgagcgacgg cctgacgtcg gcggagggaa    180
gccggcccag gctcggtgag gag                                            203

<210> SEQ ID NO 11
<211> LENGTH: 25
<212> TYPE: DNA
<213> ORGANISM: Artificial sequence
<220> FEATURE:
<223> OTHER INFORMATION: Primer

<400> SEQUENCE: 11
tgtttggaat ttagggtagt attgt                                           25

<210> SEQ ID NO 12
<211> LENGTH: 47
<212> TYPE: DNA
<213> ORGANISM: Artificial sequence
<220> FEATURE:
<223> OTHER INFORMATION: Hairpin primer

<400> SEQUENCE: 12
agcgatgcgt tcgagcatcg cutgtttgga atttagggta gtattgt                   47

<210> SEQ ID NO 13
<211> LENGTH: 24
<212> TYPE: DNA
<213> ORGANISM: Artificial sequence
<220> FEATURE:
```

```
<223> OTHER INFORMATION: Primer

<400> SEQUENCE: 13
ccatcactca ttactcaaaa caaa                                              24

<210> SEQ ID NO 14
<211> LENGTH: 24
<212> TYPE: DNA
<213> ORGANISM: Artificial sequence
<220> FEATURE:
<223> OTHER INFORMATION: Primer

<400> SEQUENCE: 14
atttttgttc ggaatttagg gtag                                              24

<210> SEQ ID NO 15
<211> LENGTH: 43
<212> TYPE: DNA
<213> ORGANISM: Artificial sequence
<220> FEATURE:
<223> OTHER INFORMATION: Hairpin primer

<400> SEQUENCE: 15
agcgatgcgt tcgagcatcg cuccgacgtc aaaccgtcgc tcg                         43

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
ccgacgtcaa accgtcgctc g                                                 21

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
cggaatttag ggtagtatcg t                                                 21

<210> SEQ ID NO 18
<211> LENGTH: 40
<212> TYPE: DNA
<213> ORGANISM: Artificial sequence
<220> FEATURE:
<223> OTHER INFORMATION: Hairpin primer

<400> SEQUENCE: 18
agcgatgcgt tcgagcatcg cuccctccgc cgacgtcaaa                             40

<210> SEQ ID NO 19
<211> LENGTH: 18
<212> TYPE: DNA
<213> ORGANISM: Artificial sequence
<220> FEATURE:
<223> OTHER INFORMATION: Primer

<400> SEQUENCE: 19
ccctccgccg acgtcaaa                                                     18

<210> SEQ ID NO 20
```

```
<211> LENGTH: 26
<212> TYPE: DNA
<213> ORGANISM: Artificial sequence
<220> FEATURE:
<223> OTHER INFORMATION: Primer

<400> SEQUENCE: 20
tagggagtat ataggtttggg gaagtt                                           26

<210> SEQ ID NO 21
<211> LENGTH: 48
<212> TYPE: DNA
<213> ORGANISM: Artificial sequence
<220> FEATURE:
<223> OTHER INFORMATION: Hairpin primer

<400> SEQUENCE: 21
agcgatgcgt tcgagcatcg cutagggagt atataggttg gggaagtt                    48

<210> SEQ ID NO 22
<211> LENGTH: 27
<212> TYPE: DNA
<213> ORGANISM: Artificial sequence
<220> FEATURE:
<223> OTHER INFORMATION: Primer

<400> SEQUENCE: 22
aacacacaat aacaaacaca aattcac                                           27

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
attttgaggg atgatcgaag                                                   20

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
ctaaaataaa acccgcctca                                                   20

<210> SEQ ID NO 25
<211> LENGTH: 15
<212> TYPE: DNA
<213> ORGANISM: Artificial sequence
<220> FEATURE:
<223> OTHER INFORMATION: Overlapping primer sequence

<400> SEQUENCE: 25
tggaatttag ggtag                                                        15

<210> SEQ ID NO 26
<211> LENGTH: 30
<212> TYPE: DNA
<213> ORGANISM: Artificial sequence
<220> FEATURE:
<223> OTHER INFORMATION: Combined primer sequence

<400> SEQUENCE: 26
```

```
attttttgttt ggaatttagg gtagtattgt                                30
```

<210> SEQ ID NO 27
<211> LENGTH: 9
<212> TYPE: PRT
<213> ORGANISM: Artificial sequence
<220> FEATURE:
<223> OTHER INFORMATION: MAGE-A3 peptide

<400> SEQUENCE: 27

Phe Leu Trp Gly Pro Arg Ala Leu Val
1               5

<210> SEQ ID NO 28
<211> LENGTH: 9
<212> TYPE: PRT
<213> ORGANISM: Artificial sequence
<220> FEATURE:
<223> OTHER INFORMATION: MAGE-A3 peptide

<400> SEQUENCE: 28

Glu Val Asp Pro Ile Gly His Leu Tyr
1               5

<210> SEQ ID NO 29
<211> LENGTH: 10
<212> TYPE: PRT
<213> ORGANISM: Artificial sequence
<220> FEATURE:
<223> OTHER INFORMATION: MAGE-A3 peptide

<400> SEQUENCE: 29

Met Glu Val Asp Pro Ile Gly His Leu Tyr
1               5                   10

<210> SEQ ID NO 30
<211> LENGTH: 10
<212> TYPE: PRT
<213> ORGANISM: Artificial sequence
<220> FEATURE:
<223> OTHER INFORMATION: MAGE-A3 peptide

<400> SEQUENCE: 30

Val His Phe Leu Leu Leu Lys Tyr Arg Ala
1               5                   10

<210> SEQ ID NO 31
<211> LENGTH: 10
<212> TYPE: PRT
<213> ORGANISM: Artificial sequence
<220> FEATURE:
<223> OTHER INFORMATION: MAGE-A3 peptide

<400> SEQUENCE: 31

Leu Val His Phe Leu Leu Leu Lys Tyr Arg
1               5                   10

<210> SEQ ID NO 32
<211> LENGTH: 10
<212> TYPE: PRT
<213> ORGANISM: Artificial sequence
<220> FEATURE:
<223> OTHER INFORMATION: MAGE-A3 peptide

<400> SEQUENCE: 32

Leu Lys Tyr Arg Ala Arg Glu Pro Val Thr
1               5                   10

-continued

```
<210> SEQ ID NO 33
<211> LENGTH: 16
<212> TYPE: PRT
<213> ORGANISM: Artificial sequence
<220> FEATURE:
<223> OTHER INFORMATION: MAGE-A3 peptide

<400> SEQUENCE: 33

Ala Cys Tyr Glu Phe Leu Trp Gly Pro Arg Ala Leu Val Glu Thr Ser
1               5                   10                  15

<210> SEQ ID NO 34
<211> LENGTH: 12
<212> TYPE: PRT
<213> ORGANISM: Artificial sequence
<220> FEATURE:
<223> OTHER INFORMATION: MAGE-A3 peptide

<400> SEQUENCE: 34

Thr Gln His Phe Val Gln Glu Asn Tyr Leu Glu Tyr
1               5                   10

<210> SEQ ID NO 35
<211> LENGTH: 20
<212> TYPE: DNA
<213> ORGANISM: Artificial sequence
<220> FEATURE:
<223> OTHER INFORMATION: Oligonucleotide

<400> SEQUENCE: 35
tccatgacgt tcctgacgtt                                              20

<210> SEQ ID NO 36
<211> LENGTH: 18
<212> TYPE: DNA
<213> ORGANISM: Artificial sequence
<220> FEATURE:
<223> OTHER INFORMATION: Oligonucleotide

<400> SEQUENCE: 36
tctcccagcg tgcgccat                                                18

<210> SEQ ID NO 37
<211> LENGTH: 30
<212> TYPE: DNA
<213> ORGANISM: Artificial sequence
<220> FEATURE:
<223> OTHER INFORMATION: Oligonucleotide

<400> SEQUENCE: 37
accgatgacg tcgccggtga cggcaccacg                                   30

<210> SEQ ID NO 38
<211> LENGTH: 24
<212> TYPE: DNA
<213> ORGANISM: Artificial sequence
<220> FEATURE:
<223> OTHER INFORMATION: Oligonucleotide

<400> SEQUENCE: 38
tcgtcgtttt gtcgttttgt cgtt                                         24

<210> SEQ ID NO 39
<211> LENGTH: 20
<212> TYPE: DNA
<213> ORGANISM: Artificial sequence
<220> FEATURE:
```

<223> OTHER INFORMATION: Oligonucleotide

<400> SEQUENCE: 39
tccatgacgt tcctgatgct                                               20

<210> SEQ ID NO 40
<211> LENGTH: 450
<212> TYPE: PRT
<213> ORGANISM: Artificial sequence
<220> FEATURE:
<223> OTHER INFORMATION: Recombinant tagged MAGE-A3

<400> SEQUENCE: 40

```
Met Asp Pro Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Met
        115                 120                 125

Asp Leu Glu Gln Arg Ser Gln His Cys Lys Pro Glu Glu Gly Leu Glu
    130                 135                 140

Ala Arg Gly Glu Ala Leu Gly Leu Val Gly Ala Gln Ala Pro Ala Thr
145                 150                 155                 160

Glu Glu Gln Glu Ala Ala Ser Ser Ser Thr Leu Val Glu Val Thr
                165                 170                 175

Leu Gly Glu Val Pro Ala Ala Glu Ser Pro Asp Pro Pro Gln Ser Pro
            180                 185                 190

Gln Gly Ala Ser Ser Leu Pro Thr Thr Met Asn Tyr Pro Leu Trp Ser
        195                 200                 205

Gln Ser Tyr Glu Asp Ser Ser Asn Gln Glu Glu Gly Pro Ser Thr
    210                 215                 220

Phe Pro Asp Leu Glu Ser Glu Phe Gln Ala Ala Leu Ser Arg Lys Val
225                 230                 235                 240

Ala Glu Leu Val His Phe Leu Leu Leu Lys Tyr Arg Ala Arg Glu Pro
                245                 250                 255

Val Thr Lys Ala Glu Met Leu Gly Ser Val Val Gly Asn Trp Gln Tyr
            260                 265                 270

Phe Phe Pro Val Ile Phe Ser Lys Ala Ser Ser Ser Leu Gln Leu Val
        275                 280                 285

Phe Gly Ile Glu Leu Met Glu Val Asp Pro Ile Gly His Leu Tyr Ile
    290                 295                 300

Phe Ala Thr Cys Leu Gly Leu Ser Tyr Asp Gly Leu Leu Gly Asp Asn
305                 310                 315                 320

Gln Ile Met Pro Lys Ala Gly Leu Leu Ile Ile Val Leu Ala Ile Ile
                325                 330                 335

Ala Arg Glu Gly Asp Cys Ala Pro Glu Glu Lys Ile Trp Glu Glu Leu
```

```
                    340                 345                 350
Ser Val Leu Glu Val Phe Glu Gly Arg Glu Asp Ser Ile Leu Gly Asp
        355                 360                 365

Pro Lys Lys Leu Leu Thr Gln His Phe Val Gln Glu Asn Tyr Leu Glu
    370                 375                 380

Tyr Arg Gln Val Pro Gly Ser Asp Pro Ala Cys Tyr Glu Phe Leu Trp
385                 390                 395                 400

Gly Pro Arg Ala Leu Val Glu Thr Ser Tyr Val Lys Val Leu His His
                405                 410                 415

Met Val Lys Ile Ser Gly Gly Pro His Ile Ser Tyr Pro Pro Leu His
                420                 425                 430

Glu Trp Val Leu Arg Glu Gly Glu Gly Gly His His His His
        435                 440                 445

His His
    450

<210> SEQ ID NO 41
<211> LENGTH: 203
<212> TYPE: DNA
<213> ORGANISM: Artificial sequence
<220> FEATURE:
<223> OTHER INFORMATION: Bisulphite converted MAGE-A3 sequence

<400> SEQUENCE: 41
tatgtttatt tttattttta tttgattttt atttaggtag aatttagttt tattttgtt      60 tggaatttag ggtagtattg ttgttaggat gtgatgttat tgatttgtgt attggaggtt    120
agaagattgt gagatttttg ttttgagtaa tgagtgatgg tttgatgttg gtggagggaa   180
gttggtttag gtttggtgag gag                                            203
```